US009340781B2

(12) United States Patent
Stuelpnagel et al.

(10) Patent No.: US 9,340,781 B2
(45) Date of Patent: *May 17, 2016

(54) COMPOSITIONS AND METHODS FOR REPRESENTATIONAL SELECTION OF NUCLEIC ACIDS FROM COMPLEX MIXTURES USING HYBRIDIZATION

(71) Applicant: Illumina, Inc., San Diego, CA (US)

(72) Inventors: John R. Stuelpnagel, San Jose, CA (US); David L. Barker, Del Mar, CA (US); Jorge Velarde, Jr., San Diego, CA (US); Steven M. Barnard, San Diego, CA (US); Michael Graige, Cardiff by the Sea, CA (US)

(73) Assignee: ILLUMINA, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/829,152

(22) Filed: Aug. 18, 2015

(65) Prior Publication Data
US 2015/0353998 A1     Dec. 10, 2015

Related U.S. Application Data

(63) Continuation of application No. 14/536,354, filed on Nov. 7, 2014, now Pat. No. 9,139,826, which is a continuation of application No. 14/046,859, filed on Oct. 4, 2013, now Pat. No. 8,916,350, which is a continuation of application No. 12/445,069, filed as application No. PCT/US2007/018687 on Aug. 24, 2007, now Pat. No. 8,568,979.

(60) Provisional application No. 60/850,854, filed on Oct. 10, 2006.

(51) Int. Cl.
C12Q 1/68 (2006.01)
C12N 15/10 (2006.01)

(52) U.S. Cl.
CPC .......... *C12N 15/1072* (2013.01); *C12Q 1/6837* (2013.01)

(58) Field of Classification Search
None
See application file for complete search history.

(56) References Cited

U.S. PATENT DOCUMENTS

| | | | |
|---|---|---|---|
| 5,200,314 A | 4/1993 | Urdea | |
| 5,302,509 A | 4/1994 | Cheeseman | |
| 5,324,632 A | 6/1994 | Weisburg et al. | |
| 5,714,380 A | 2/1998 | Neri et al. | |
| 5,750,338 A | 5/1998 | Colins et al. | |
| 5,780,224 A | 7/1998 | Collins | |
| 6,013,440 A | 1/2000 | Lipshutz et al. | |
| 6,268,133 B1 | 7/2001 | Nisson et al. | |
| 6,306,597 B1 | 10/2001 | Macevicz | |
| RE37,891 E | 10/2002 | Collins et al. | |
| 6,534,273 B2 | 3/2003 | Weisburg et al. | |
| 6,632,611 B2 | 10/2003 | Su et al. | |
| 7,214,490 B2 | 5/2007 | Su et al. | |
| 7,217,522 B2 | 5/2007 | Brenner | |
| 7,320,862 B2 | 1/2008 | Stahler et al. | |
| 7,393,665 B2 | 7/2008 | Brenner | |
| 7,407,757 B2 | 8/2008 | Brenner | |
| 8,568,979 B2 | 10/2013 | Stuelpnagel et al. | |
| 8,916,350 B2 | 12/2014 | Stuelpnagel et al. | |

(Continued)

FOREIGN PATENT DOCUMENTS

| | | |
|---|---|---|
| EP | 0 328 829 | 8/1989 |
| EP | 1 184 466 | 3/2002 |

(Continued)

OTHER PUBLICATIONS

Final Office Action for U.S. Appl. No. 11/599,605 mailed Dec. 2, 2008.

(Continued)

*Primary Examiner* — James Martinell

(74) *Attorney, Agent, or Firm* — Brent C. Moore; Illumina, Inc.

(57) ABSTRACT

The invention provides a method of selecting a representational sample of nucleic acid sequences from a complex mixture. The method includes: (a) contacting a complex mixture of nucleic acids under conditions sufficient for hybridization with a population of capture probes complementary to one or more nucleic acids comprising a predetermined portion of the sequence collectively present in the complex mixture to form hybridization complexes of the one or more nucleic acids with the population of probes, the population of capture probes being attached to a solid support, and (b) removing unhybridized nucleic acids to select a representational sample of nucleic acids having a complexity of less than 10% but more than 0.001% of the complex mixture, wherein the representational sample comprises a nucleic acid copy having a proportion of each sequence in the copy relative to all other sequences in the copy substantially the same as the proportions of the sequences in the predetermined portion of one or more nucleic acids within the complex mixture. A method of selecting a representational sample of genomic sequences from a complete genome also is provided. The invention further provides a nucleic acid population that includes a representational sample having a complexity of less than 10% but more than 0.001% of a complex mixture, the representational sample comprising a nucleic acid copy having a proportion of each sequence in the copy relative to all other sequences in the copy substantially the same as the proportions of sequences in a predetermined portion of a sequence collectively present in one or more nucleic acids within the complex mixture.

20 Claims, No Drawings

(56) References Cited

U.S. PATENT DOCUMENTS

| | | |
|---|---|---|
| 2002/0119455 A1 | 8/2002 | Chan |
| 2003/0044822 A1 | 3/2003 | Fletcher et al. |
| 2003/0082543 A1 | 5/2003 | Su et al. |
| 2003/0211489 A1 | 11/2003 | Shen |
| 2005/0009020 A1 | 1/2005 | Distler |
| 2005/0181408 A1 | 8/2005 | Brenner |
| 2006/0063168 A1 | 3/2006 | Albertson et al. |
| 2006/0270059 A1 | 11/2006 | Huang et al. |
| 2006/0286570 A1 | 12/2006 | Rowlen et al. |
| 2007/0009954 A1 | 1/2007 | Wang et al. |
| 2007/0042400 A1 | 2/2007 | Choi et al. |
| 2007/0042419 A1 | 2/2007 | Barany et al. |
| 2007/0099195 A1 | 5/2007 | Huang et al. |

FOREIGN PATENT DOCUMENTS

| | | |
|---|---|---|
| WO | 98/44151 | 10/1998 |
| WO | 99/23256 | 5/1999 |
| WO | 00/06770 | 2/2000 |
| WO | 00/18957 | 4/2000 |
| WO | 01/06014 | 1/2001 |
| WO | 01/12862 | 2/2001 |
| WO | 01/46470 | 6/2001 |
| WO | 01/57284 | 8/2001 |
| WO | 02/06528 | 1/2002 |
| WO | 02/083943 | 10/2002 |
| WO | 03/048387 | 6/2003 |
| WO | 2004/018493 | 3/2004 |
| WO | 2004/018497 | 3/2004 |
| WO | 2005/089110 | 9/2005 |
| WO | 2006/064199 | 6/2006 |
| WO | 2007/057652 | 5/2007 |
| WO | 2007/092538 | 8/2007 |
| WO | 2007/136736 | 11/2007 |
| WO | 2007136833 | 11/2007 |
| WO | 2008/033442 | 3/2008 |

OTHER PUBLICATIONS 3.3 Paper III, "Inversion of in situ synthesized oligonucleotides: improved reagents for hybridization and primer extension in DNA microarrays", retrieved from Internet: uu.diva-portal.org/smash/get/diva2:162051/FULLTEXT01, 2002, 24-25.

Affymetrix, "GeneChip HuSNP Mapping Assay", Affymetrix Catalog, GeneChip HuSNP Mapping Assay, 2001, 1-4.

Brenner, "Gene Expression Analysis by Massively Parallel Signature Sequencing (MPSS) on Microbead Arrays", Nature Biotechnology, vol. 18, 2000, 630-634.

Gill, et al., "Genome-wide screening for train conferring genes using DNA microarrays", PNAS 99, 2002, 7033-7038.

Kandpal, et al., "Selective enrichment of a large size genomic DNA fragment by affinity capture: an approach for genome mapping", Nucleic Acids Research 18, 1990, 1789-1795.

Margulies, et al., "Genome sequencing in microfabricated high-density picolitre reactors", Nature, vol. 437, 2005, 376-380 and Supplemental Materials.

Morgan, et al., "The selective isolation of novel cDNAs encoded by the regions surrounding the human interleukin 4 and 5 genes", Nucleic Acids Research 20, 1992, 5173-5179.

Shendure, et al., "Accurate Multiplex Polony Sequencing of an Evolved Bacterial Genome", Science, vol. 309, Sep. 9, 2005, 1728-1732.

Welcher, et al., "Selective enrichment of specific DNA, cDNA and RNA sequences using biotinylated probes, advidin and copper-chelate agarose", Nucleic Acids Research 14, 1986, 100027-10044.

Zhang, Ji-Hong et al., "Reconstruction of DNA sequencing by hybridization", Bioinformatics, vol. 19 No. 1, 2003, 14-21.

COMPOSITIONS AND METHODS FOR REPRESENTATIONAL SELECTION OF NUCLEIC ACIDS FROM COMPLEX MIXTURES USING HYBRIDIZATION

BACKGROUND OF THE INVENTION

This invention relates generally to methods for high throughput isolation and analysis of nucleic acids and, more specifically to genomic sequence analysis useful in personalized medical analysis.

The diagnosis and treatment of human diseases continues to be a major area of social concern. The importance of improving health care is self evident; so long as there continues to be diseases that affect individuals, there will be an effort to understand the cause of such diseases as well as efforts to diagnose and treat such diseases. Preservation of life is an inherent force motivating the vast amount of time and expenditure continually invested into scientific discovery and development processes. The application of results from these scientific processes to the medical field has led to surprising advancements in diagnosis and treatment over the last century, and especially over the last quarter century. Such advancements have improved both the quality of life and life span of affected individuals.

However significant in both scientific and medical contribution to their respective fields, the progression of advancements have been slow and painstaking, generally resulting from step wise trial and error hypothesis driven research. Moreover, with each advancement there can be cumulative progression in the overall scientific understanding of a problem, but there are few guarantees that the threshold needed to translate a discovery into a practical medical application has been achieved. Additionally, with the achievement of all too many advancements comes the sobering realization that the perceived final answer for a complete understanding of a particular physiological or biochemical process is, instead, just a beginning to a more complex process still needed to be dissected and understood.

Further complicating the progression of scientific advancements and its practical application can result from technical limitations in available methodology. Each discovery or advancement can push the frontiers of science to new extremes. Many times, continued progress can be stalled due to the unavailability or insufficiency in technological sophistication needed to continue studies or implement practical applications at the new extremes. Therefore, further advancements in the scientific discovery and medical fields necessarily have to await progress in other fields for the advent and development of more capable technologies and materials. As a result, the progression of scientific advancements having practical diagnostic and therapeutic applications can occur relatively slowly because it results from the accumulation of many smaller discoveries, contributions and advancements in technologies.

Genomic technology has been one such scientific advancement purported to open new avenues into the discovery and development processes and achieve new dimensions in the medical diagnostic and therapeutic fields. Genomic research has resulted in the sequencing of numerous whole genomes, including human. Futuristic speculation of genomic technology for medical applications has been directed to revolutionary diagnostic applications because of the precise physical characteristics purportedly available from complete genome sequences.

However, except for certain nucleic acid detection procedures amenable to selected targets, application of the vast amount of genomic information and technology to medical diagnosis and treatment is still in its infancy. One drawback hindering the application of genomics to practical medicine is due to the inability to select relevant sequences among a vast amount of non-informative sequences for analysis. In effect, the wheat cannot be sufficiently separated from the chaff prior to analysis, which leads to bias in the results.

For example, one problem with many nucleic acid selection methods is the loss of an accurate sequence representation in the selected population compared to the authentic genomic population. Selection methods amenable to medical applications generally amplify specific regions of the nucleic acids using a variety of methods including, for example, PCR, rolling circle, TMA, NASBA and the like. However, batch amplification needed for high throughput genomic applications results in significant distortion of the resulting sequence representation compared to the original mixture.

An alternative method for selecting nucleic acids from complex genomic mixtures employs destruction of the unwanted nucleic acid. These methods often rely on chemistries of specific bases or sequences and have limited applicability to large scale and/or high throughput analysis because of their inability to target any region of the genome. Therefore, while spectacular in its potential ramifications, the ability to accurately sort through, select and identify relevant genomic sequences among other genomic sequences in complex genomic DNA mixture has failed to allow application of this technology to achieve its potential.

Thus, there exists a need for a nucleic acid selection method applicable to complex mixtures such as genomic DNA that provides an accurate representation of sequences within the original mixture. The present invention satisfies this need and provides related advantages as well.

SUMMARY OF THE INVENTION

The invention provides a method of selecting a representational sample of nucleic acid sequences from a complex mixture. The method includes: (a) contacting a complex mixture of nucleic acids under conditions sufficient for hybridization with a population of capture probes complementary to one or more nucleic acids comprising a predetermined portion of the sequence collectively present in the complex mixture to form hybridization complexes of the one or more nucleic acids with the population of probes, the population of capture probes being attached to a solid support, and (b) removing unhybridized nucleic acids to select a representational sample of nucleic acids having a complexity of less than 10% but more than 0.001% of the complex mixture, wherein the representational sample comprises a nucleic acid copy having a proportion of each sequence in the copy relative to all other sequences in the copy substantially the same as the proportions of the sequences in the predetermined portion of one or more nucleic acids within the complex mixture. A method of selecting a representational sample of genomic sequences from a complete genome also is provided. The invention further provides a nucleic acid population that includes a representational sample having a complexity of less than 10% but more than 0.001% of a complex mixture, the representational sample comprising a nucleic acid copy having a proportion of each sequence in the copy relative to all other sequences in the copy substantially the same as the proportions of sequences in a predetermined portion of a sequence collectively present in one or more nucleic acids within the complex mixture.

DETAILED DESCRIPTION OF THE INVENTION

This invention is directed to representational selection of nucleic acids from a complex mixture. The nucleic acids include DNA, such as genomic DNA (gDNA) or cDNA, or RNA, such as messenger RNA (mRNA). Representational selection can be used to obtain a sample having complexity substantially equivalent to the nucleic acid mixture or to obtain a subsample having desired lower level of complexity. Selection of subsamples allows for the separation of informative sequences from the less informative sequences that contribute to distortion and/or bias in subsequent analysis. The subsample can be any desired representation of sequences within a complex mixture. One particularly useful subsample consists of an accurate representation of unique sequences within a genome or within a portion of a genome. Such a sample represents a genomic blueprint of the sequence composition devoid of distortions or variance due to sequence copy number. Such a single copy genomic blueprint is particularly useful in diagnostic and other medical applications because it reduces the required sequence coverage necessary for subsequent analysis by eliminating sequence redundancy.

In one embodiment, the method of the invention selects a subsample of nucleic acids from a complex genomic mixture representing all unique sequences of a genome. Such a subsample will correspond to the DNA complexity of the target genome. In other embodiments, the method of the invention selects representational samples of nucleic acid sequences from a complex mixture corresponding to a desired fraction of the nucleic acids within the mixture to reduce sequence variance and subsequent coverage in downstream assays. The desired fraction can be, for example, an arbitrary percentage or a percentage based on known or estimated characteristics of the target genomic region. In certain embodiments, the desired fraction of sequences for a representational sample can be, for example, <0.01%, 0.01% 0.1%, 1%, 5%, 20% and the like.

In other embodiments, one particularly useful characteristic of representational selection is that by reducing the variance incurred in the sequence selection method, one may reduce the fold coverage necessary to sequence a specific region, and consequently reduce the cost of the sequencing. Reduction of variance due to complex sequence characteristics of large populations incurred in the selection method also allows more accurate quantification of particular nucleic acids within the population. The lower the variance incurred in a sequence selection method the more accurate the quantification of constituent sequences. This characteristic is particularly useful when looking at rare events such as a rare mutation or a low copy number gene.

Accordingly, in further specific embodiments, a representational sample selected from a complex mixture is used in subsequent downstream analysis for delivery of more accurate and less biased results. One analysis method applicable with a representational sample of the invention is sequence determination including, for example, targeted resequencing of genomic regions, specific genes, exons genetically conserved regions, methylated regions, or other areas of interest. Other subsequent analysis methods applicable with a representational sample of the invention include, for example, determination of tumor or pathogenic cell number or percentage in a mixed cell population by accurately quantifying mutations indicative of cancer or other pathogenesis. Another subsequent analysis method applicable for use with a representational sample of the invention includes digital gene expression, where expression of a targeted set of genes is desired. In this specific embodiment, expressed RNA is converted into cDNA and specific transcripts selected from the complex mixture consisting of the total cDNA pool.

In one specific embodiment of the method of the invention, pools of microspheres are attached to polynucleotide capture probes. The capture probes are designed to specifically hybridize to target regions of nucleic acids in a complex mixture. Target regions are captured and the non-captured sequences removed by washing. Captured sequences are eluted and available for use in subsequent downstream analysis. One alternative employs a single capture probe sequence or species attached to each microsphere. Another alternative employs the attachment of different capture probe species or chimeric species to each microsphere. Other specific embodiments employ solid supports other than microspheres for capture probe attachment including, for example, planar surfaces such as arrays or microspheres positioned within an array.

As used herein, the term "complex mixture" when used in reference to nucleic acids of the invention is intended to refer to a plurality of different nucleic acids or nucleic acid sequences composed of many varied and separable parts or constituents. Therefore, the term as it is used herein refers to a plurality of nucleic acids having relative diversity in its constituent sequences. Diversity can be relative to sequences of other nucleic acid molecules within the plurality, relative to sequences of portions of nucleic acids within the plurality or relative to a referenced standard. A complex mixture includes pluralities having high, medium or low sequence complexity, sequence copy number or both. Separable parts or constituents of a complex mixture of the invention refers to components of the whole that are analyzable or decipherable apart from the referenced plurality. Such constituents include, for example, genomic structures, gene structural organization, genes, gene segments, intervening sequences between genes, coding regions, open reading frames, exons, introns, untranslated regions, regulatory regions, promoter regions and the like. Exemplary complex nucleic acid mixtures include, but are not limited to, a genome, a chromosome or a collection of chromosomes making up a genome or portion of a genome.

Particular forms of nucleic acids comprising a complex mixture of the invention include all types of nucleic acids found in an organism. In particular, a complex mixture of nucleic acids of the invention can include, for example, genomic DNA (gDNA), populations of genomic nucleic acids and/or populations of nucleic acids corresponding to genes, such as gene structural regions or expressed sequences, such as expressed sequence tags (ESTs), DNA copied messenger RNA (cDNA), RNA copied messenger RNA (cRNA), mitochondrial DNA or genome, RNA, messenger RNA (mRNA) and/or other populations of RNA. Nucleotide sequence information for any of the above exemplary forms of nucleic acids can be obtained from, for example, sequence databases, publications or directly from raw sequence data.

The methods set forth herein are useful for analysis of large genomes such as those typically found in eukaryotic unicellular and multicellular organisms. Exemplary eukaryotic nucleic acid mixtures that can be used in a method set forth herein includes, without limitation, that from a mammal such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *dictyostelium discoideum*; a fungi such as *pneumocystis carinii, Takifugu rubripes*, yeast, *Saccharamoyces cerevisiae* or *Schizosaccharomyces pombe*; or a *plasmodium falciparum*. The methods can also be used with nucleic acid mixtures from organisms having smaller genomes such as those from a prokaryote such as a bacterium, *Escherichia coli, staphylococci* or *mycoplasma pneumoniae*; an archae; a virus such as Hepatitis C virus or human immunodeficiency virus; or a viroid.

A nucleic acid mixture can be isolated from one or more cells, bodily fluids or tissues. Known methods can be used to obtain a bodily fluid such as blood, sweat, tears, lymph, urine, saliva, semen, cerebrospinal fluid, feces or amniotic fluid. Similarly known biopsy methods can be used to obtain cells or tissues such as buccal swab, mouthwash, surgical removal, biopsy aspiration or the like. Nucleic acids can also be obtained from one or more cell or tissue in primary culture, in a propagated cell line, a fixed archival sample, forensic sample, fresh frozen paraffin embedded sample or archeological sample.

Exemplary cell types from which nucleic acids can be obtained include, without limitation, a blood cell such as a B lymphocyte, T lymphocyte, leukocyte, erythrocyte, macrophage, or neutrophil; a muscle cell such as a skeletal cell, smooth muscle cell or cardiac muscle cell; germ cell such as a sperm or egg; epithelial cell; connective tissue cell such as an adipocyte, fibroblast or osteoblast; neuron; astrocyte; stromal cell; kidney cell; pancreatic cell; liver cell; or keratinocyte. A cell from which gDNA is obtained can be at a particular developmental level including, for example, a hematopoietic stem cell or a cell that arises from a hematopoietic stem cell such as a red blood cell, B lymphocyte, T lymphocyte, natural killer cell, neutrophil, basophil, eosinophil, monocyte, macrophage, or platelet. Other cells include a bone marrow stromal cell (mesenchymal stem cell) or a cell that develops therefrom such as a bone cell (osteocyte), cartilage cells (chondrocyte), fat cell (adipocyte), or other kinds of connective tissue cells such as one found in tendons; neural stem cell or a cell it gives rise to including, for example, a nerve cells (neuron), astrocyte or oligodendrocyte; epithelial stem cell or a cell that arises from an epithelial stem cell such as an absorptive cell, goblet cell, Paneth cell, or enteroendocrine cell; skin stem cell; epidermal stem cell; or follicular stem cell. Generally any type of stem cell can be used including, without limitation, an embryonic stem cell, adult stem cell, or pluripotent stem cell.

As most naturally occurring nucleic acids derive from genomic nucleic acid, a reference to a specific type of nucleic acid sequence is intended to refer to a subcategory of a genomic nucleic acid sequence. Similarly, and unless specifically referred to otherwise, the use of the general term "nucleic acid" without reference to genomic or a subcategory thereof of genetic information is intended to include both naturally occurring and non-naturally occurring nucleic acids or nucleotide sequences. For example, genomic sequences can contain genetic structural regions, such as a gene, including exons, introns, promoters, 5' untranslated regions (UTRs), 3' UTRs or other substructures thereof, intragenic region sequence, centromeric region sequence, or telomeric region sequence, as well as other chromosomal regions well known to those skilled in the art.

A genomic DNA used in the invention can have one or more chromosomes. For example, a prokaryotic genomic DNA including one chromosome can be used. Alternatively, a eukaryotic genomic DNA including a plurality of chromosomes can be used in a method disclosed herein. Thus, the methods can be used, for example, to select, amplify or analyze a genomic DNA having n equal to 2 or more, 4 or more, 6 or more, 8 or more, 10 or more, 15 or more, 20 or more, 23 or more, 25 or more, 30 or more, or 35 or more chromosomes, where n is the haploid chromosome number and the diploid chromosome count is 2n. The size of a genomic DNA used in a method of the invention can also be measured according to the number of base pairs or nucleotide length of the chromosome complement. Exemplary size estimates for some of the genomes that are useful in the invention are about 3.1 Gbp (human), 2.7 Gbp (mouse), 2.8 Gbp (rat), 1.7 Gbp (zebrafish), 165 Mbp (fruitfly), 13.5 Mbp (*S. cerevisiae*), 390 Mbp (fugu), 278 Mbp (mosquito) or 103 Mbp (*C. elegans*). Those skilled in the art will recognize that genomes having sizes other than those exemplified above including, for example, smaller or larger genomes, can be used.

While the invention is exemplified by reference to nucleic acids for purposes of illustration, given the teachings and guidance provided herein, those skilled in the art will understand that the methods and compositions of the invention are equally applicable to complex mixtures of biopolymers other than nucleic acids. In particular, those skilled in the art can routinely employ the compositions and methods of the invention to select representational samples of sequences or biopolymer species from complex mixtures of, for example, polypeptides, polysaccharides and/or lipids.

Also for ease of illustration the methods are typically exemplified herein for nucleic acid mixtures obtained from a single cell type. It will be understood that nucleic acid mixtures can be obtained from a mixed cell sample having two or more different cell types. The different cell types can be from a single multicellular organism including, for example, a tissue having cells that are differently affected by cancer or some other disease or condition. Similarly, a mixed cell sample can be obtained from a biopsy sample having cells from a host as well as one or more parasite or an ecological sample having multiple different organisms from a particular environment. Accordingly, quantitative analyses such as those set forth in further detail below can be used to determine the quantity and types of cells present in a mixture of cells.

As used herein, the term "representational," when used in reference to a sample of nucleic acids selected from a complex mixture of nucleic acids, is intended to mean a nucleic acid sample in which the proportion of each sequence in the sample relative to all other sequences in the sample is substantially the same as the proportions in the nucleic acids in the complex mixture. In particular embodiments, the sample is obtained by copying or amplification such that the proportion of each sequence in the copy relative to all other sequences in the copy is substantially the same as the proportions in the nucleic acids in the complex mixture. A nucleic acid copy can be a single molecule or plurality of molecules such as fragments that are smaller than the nucleic acids of the complex mixture. Accordingly, the proportion of different fragments in the population will be substantially the same as the proportion of their sequences in the reference complex mixture. Substantial similarity between the proportion of sequences in a representational nucleic acid copy or sample and one or more nucleic acids of a complex mixture means that at least 90% of the loci in the copy are no more than 2-fold over-represented or under-represented compared to the template. Other percentages and ranges of representation also are included in the meaning of the term as exemplified further below. For example, the sample can have high complexity or low complexity as set forth in further detail below. The amount of fold over-representation or under-representation can differ depending upon the type of analysis desired. A lower value, such as no more than 5-fold, 4-fold, 3-fold or 2-fold over-representation or under-representation favors more quantitative methods such as sequencing application where fold coverage is relatively low. However, a larger range can be acceptable for other analysis methods such as sequencing using higher fold coverage. Exemplary values include, but are not necessarily bounded by, no more than 10-fold, 15-fold, 20-fold, 25-fold or 50-fold over-representation or under-representation.

A representational sample of a nucleic acid can have a complexity that includes all or part of the sequence present in a complex mixture or in a predetermined portion of nucleic acids within a complex mixture. The part of the sequence of the complex mixture or predetermined portion of nucleic acids within a complex mixture that is included in a representational copy can be a single contiguous portion of the template such as an arm of a chromosome. Alternatively, the part of the sequence of the complex mixture or predetermined portion of nucleic acids within a complex mixture that is included in a representational copy can be several portions of the mixture or portion of nucleic acids such as a plurality of exons or genes of a genome. Accordingly, the portions need not be contiguous in comparison with the sequence of the complex mixture or predetermined portion of nucleic acids within a complex mixture. For example, a representational copy of a genome can include a plurality of exon sequences and exclude intron sequences and other intervening sequences, or a representational copy can include a plurality of gene sequences while excluding intervening sequences that occur between the genes in the genome sequence. Therefore, a representational sample of the invention can include, for example, a copy that substantially approximates sequence copy number, sequence complexity or both number and sequence complexity of the reference complex mixture or portion thereof.

The term "high complexity copy" refers to a nucleic acid copy having at least about 50% of the unique sequence of its cognate, original complex mixture or predetermined portion of nucleic acids within its cognate, original complex mixture. Thus, a high complexity representation of a complex mixture or predetermined portion of nucleic acids can include, without limitation, at least about 60%, 70%, 75%, 80%, 85%, 90%, 95% or 99% of the sequence of the authentic complex mixture or predetermined portion of nucleic acids of the authentic complex mixture. The term "low complexity copy" refers to a nucleic acid copy having at most about 49% of the unique sequence of its cognate, original complex mixture or predetermined portion of nucleic acids within its cognate, original complex mixture. Thus, a low complexity representation of a complex mixture or predetermined portion of nucleic acids can include, without limitation, at most about 49%, 40%, 30%, 20%, 10%, 5%, 1%, 0.5%, 0.1%, 0.05%, 0.01%, 0.005%, 0.001% or less of the sequence of the authentic complex mixture or predetermined portion of nucleic acids of the authentic complex mixture. In particular embodiments, a nucleic acid copy can have a complexity representing at least about 0.1%, 1%, 5%, 10%, 20%, 30%, or 40% of the sequence of the authentic complex mixture or predetermined portion of nucleic acids of the authentic complex mixture. In other embodiments, a nucleic acid copy can have a complexity within a range of the above exemplary levels. For example, a nucleic acid copy can have a complexity less than 10% but more than 0.001%, or between 0.001% and 1%. Other complexities levels and/or ranges are included within the meaning of these terms as illustrated by the above complexity level and ranges and as exemplified further below.

The term "veritable" when used in reference to a representational population of nucleic acids or nucleic acid sequences refers to a population of nucleic acids or sequences having at least one characteristic substantially similar or proportional to a characteristic of the nucleic acids or nucleic acid sequences within the referenced population or complex mixture. A characteristic includes, for example, nucleotide sequence similarity, population complexity, sequence complexity, copy number or combinations thereof. Characteristics that are proportional include, for example, ratios of gene frequency or copy number or percent coverage of a nucleic acid region. Therefore, the term as it is used herein refers to a population of nucleic acids or sequences having a sequence characteristic not unlike the constituents of the nucleic acids or sequences of the referenced population. A veritable population includes, for example, a substantially similar representation or a true copy or replica of the nucleic acids or sequences constituting the authentic complex mixture. The term "veritable" also refers to a representation of a subset of nucleic acids or sequences within a referenced population such as a complex mixture. Such a subset of includes, for example, unique sequences within the complex mixture and/or the frequency of occurrence of unique sequences or both the unique sequence representation and the frequency of occurrence of unique sequences within a referenced population such as a complex mixture.

As used herein, the term "capture probe" is intended to mean a polynucleotide having sufficient complementarity to specifically hybridize to a target nucleic acid. A capture probe functions as an affinity binding molecule for isolation of a target nucleic acid from other nucleic acids and/or components in a mixture. Capture probes of the invention are attached, or can be modified to attach, to a solid support. Capture probes can be of any desired length and/or sequence so long as they exhibit sufficient complementarity to specifically hybridize to a target nucleic acid for capture and isolation from other components in a mixture. A target nucleic acid specifically bound by a capture probe can be a nucleic acid within a complex mixture. A target nucleic acid also can be specifically bound by a capture probe through intervening molecules such as linkers, adapters and other bridging nucleic acids having sufficient complementarity to specifically hybridize to both a target sequence and a capture probe. In the former example, a capture probe directly hybridizes to the target nucleic acid. In the latter example, a capture probe indirectly hybridizes, through a secondary hybridization reaction, to the target nucleic acid. Methods and probe components for a variety of nucleic acid capture and isolation formats are well known to those skilled in the art.

A capture probe or other nucleic acid used in a method of the invention can have any of a variety of compositions or sizes, so long as it has the ability to hybridize to a template nucleic acid with sequence specificity. Accordingly, a nucleic acid having a native structure or an analog thereof can be used. A nucleic acid with a native structure generally has a backbone containing phosphodiester bonds and can be, for example, deoxyribonucleic acid or ribonucleic acid. An analog structure can have an alternate backbone including, without limitation, phosphoramide, phosphorothioate, phosphorodithioate, O-methylphophoroamidite linkages, and peptide nucleic acid backbones and. Other analog structures include those with positive backbones (see, for example, Dempcy et al., *Proc. Natl. Acad. Sci. USA* 92:6097 (1995); non-ionic backbones (see, for example, U.S. Pat. Nos. 5,386,023, 5,637, 684, 5,602,240, 5,216,141 and 4,469,863; Kiedrowshi et al., *Angew. Chem. Intl. Ed. English* 30:423 (1991); Letsinger et al., *J. Am. Chem. Soc.* 110:4470 (1988); Letsinger et al., *Nucleoside & Nucleotide* 13:1597 (1994); Chapters 2 and 3, ASC Symposium Series 580, "Carbohydrate Modifications in Antisense Research", Ed. Y. S. Sanghui and P. Dan Cook; Mesmaeker et al., *Bioorganic & Medicinal Chem. Lett.* 4:395 (1994); Jeffs et al., *J. Biomolecular NMR* 34:17 (1994) and non-ribose backbones, including, for example, those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Analog structures containing one or more carbocyclic sugars are also useful in the methods and are described, for example, in Jenkins et al., Chem. Soc. Rev. (1995) pp 169-176. Several other analog structures that are useful in the invention are described in Rawls, C & E News Jun. 2, 1997 page 35. Each of the above references is incorporated herein by reference.

Native DNA used in the invention typically has one or more bases selected from the group consisting of adenine, thymine, cytosine, methyl cytosine or guanine and RNA can have one or more bases selected from the group consisting of uracil, adenine, cytosine or guanine. Exemplary non-native bases that can be included in a nucleic acid, whether having a native backbone or analog structure, include, without limitation, inosine, xathanine, hypoxathanine, isocytosine, isoguanine, 5-methylcytosine, 5-hydroxymethyl cytosine, 2-aminoadenine, 6-methyl adenine, 6-methyl guanine, 2-propyl guanine, 2-propyl adenine, 2-thioLiracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. A particular embodiment can utilize isocytosine and isoguanine in a nucleic acid in order to reduce non-specific hybridization, as generally described in U.S. Pat. No. 5,681, 702. Examples of these and other nucleic acids including analogs, and examples of their use in hybridization methods are described, for example, in US 2005/0181394, which is incorporated herein by reference.

Following the teachings and guidance provided herein, those skilled in the art will understand that different capture probes will have different primary nucleotide sequences and will exhibit different hybridization specificities. Accordingly, a capture probe specific for a first nucleic acid will have a different primary sequence compared to a capture probe specific for a second nucleic acid. Similarly, the terms "first," "second," "third" and any such following numbers refer to different nucleic acids having different nucleotide sequences.

As used herein, the term "population" is intended to mean two or more different nucleic acids having different nucleotide sequences. Therefore, a population constitutes a plurality of two or more different members. Populations can range in size from small, medium, large, to very large. The size of small populations can range, for example, from a few members to tens of members. Medium populations can range, for example, from tens of members to about 100 members or hundreds of members. Large populations can range, for example, from about hundreds of members to about 1000 members, to thousands of members and up to tens of thousands of members. Very large populations can range, for example, from tens of thousands of members to about hundreds of thousands, a million, millions, tens of millions and up to or greater than hundreds of millions members. Therefore, a population can range in size from two to well over one hundred million members as well as all sizes, as measured by the number of members, in between and greater than the above exemplary ranges. A specific example of a large population is a plurality of capture probes of about $5\times10^5$, which corresponds to the number of genes contained in the human genome. A further specific example of a population of capture probes of the invention is a plurality of probes corresponding to the DNA complexity of the human genome. Accordingly, the definition of the term is intended to include all integer values greater than two. An upper limit of a population of the invention can be set, for example, by the theoretical diversity of nucleotide sequences in a complex mixture of the invention.

As used herein, the term "predetermined" is intended to mean that the referenced nucleic acid, nucleic acid portion, nucleic acid region or nucleotide sequence is known or characterized. Therefore, a population of capture probes having nucleic acid sequences for a predetermined nucleic acid refers to probes that have been prior selected to be complementary to the predetermined sequence or sequences.

As used herein, the term "solid support" is intended to mean a substrate and includes any material that can serve as a solid or semi-solid foundation for attachment of capture probes, other nucleic acids and/or other polymers, including biopolymers. A solid support of the invention is modified, for example, or can be modified to accommodate attachment of nucleic acids by a variety of methods well known to those skilled in the art. Exemplary types of materials comprising solid supports include glass, modified glass, functionalized glass, inorganic glasses, microspheres, including inert and/or magnetic particles, plastics, polysaccharides, nylon, nitrocellulose, ceramics, resins, silica, silica-based materials, carbon, metals, an optical fiber or optical fiber bundles, a variety of polymers other than those exemplified above and multiwell microtier plates. Specific types of exemplary plastics include acrylics, polystyrene, copolymers of styrene and other materials, polypropylene, polyethylene, polybutylene, polyurethanes and Teflon™. Specific types of exemplary silica-based materials include silicon and various forms of modified silicon.

The term "microsphere," "bead" or "particle" refers to a small discrete particle as a solid support of the invention. Populations of microspheres can be used for attachment of populations of capture probes. The composition of a microsphere can vary, depending for example, on the format, chemistry and/or method of attachment and/or on the method of nucleic acid synthesis. Exemplary microsphere compositions include solid supports, and chemical functionalities imparted thereto, used in polypeptide, polynucleotide and/or organic moiety synthesis. Such compositions include, for example, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and Teflon™, as well as any other materials which can be found described in, for example, *"Microsphere Detection Guide"* from Bangs Laboratories, Fishers Ind.

Similar to a microsphere composition, the geometry of a microsphere also can correspond to a wide variety of different forms and shapes. For example, microspheres used as solid supports of the invention can be spherical, cylindrical or any other geometrical shape and/or irregularly shaped particles. In addition, microspheres can be, for example, porous, thus increasing the surface area of the microsphere available for capture probe or other nucleic acid attachment. Exemplary sizes for microspheres used as solid supports in the methods and compositions of the invention can range from nanometers to millimeters or from about 10 nm-1 mm. Particularly useful sizes include microspheres from about 0.2 µm to about 200 µm and from about 0.5 µm to about 5 µm being particularly useful.

In particular embodiments, microspheres or beads can be arrayed or otherwise spatially distinguished. Exemplary bead-based arrays that can be used in the invention include, without limitation, those in which beads are associated with a solid support such as those described in U.S. Pat. No. 6,355, 431 B1, US 2002/0102578 and PCT Publication No. WO 00/63437. Beads can be located at discrete locations, such as wells, on a solid-phase support, whereby each location accommodates a single bead. Alternatively, discrete locations where beads reside can each include a plurality of beads as described, for example, in U.S. patent application Nos. US 2004/0263923, US 2004/0233485, US 2004/0132205, or US 2004/0125424. Beads can be associated with discrete locations via covalent bonds or other non-covalent interactions such as gravity, magnetism, ionic forces, van der Waals forces, hydrophobicity or hydrophilicity. However, the sites of an array of the invention need not be discrete sites. For example, it is possible to use a uniform surface of adhesive or chemical functionalities that allows the attachment of particles at any position. Thus, the surface of an array substrate can be modified to allow attachment or association of microspheres at individual sites, whether or not those sites are contiguous or non-contiguous with other sites. Thus, the surface of a substrate can be modified to form discrete sites such that only a single bead is associated with the site or, alternatively, the surface can be modified such that a plurality of beads populates each site.

Beads or other particles can be loaded onto array supports using methods known in the art such as those described, for example, in U.S. Pat. No. 6,355,431. In some embodiments, for example when chemical attachment is done, particles can be attached to a support in a non-random or ordered process. For example, using photoactivatible attachment linkers or photoactivatible adhesives or masks, selected sites on an array support can be sequentially activated for attachment, such that defined populations of particles are laid down at defined positions when exposed to the activated array substrate. Alternatively, particles can be randomly deposited on a substrate. In embodiments where the placement of probes is random, a coding or decoding system can be used to localize and/or identify the probes at each location in the array. This can be done in any of a variety of ways, for example, as described in U.S. Pat. No. 6,355,431 or WO 03/002979. A further encoding system that is useful in the invention is the use of diffraction gratings as described, for example, in US Pat. App. Nos. US 2004/0263923, US 2004/0233485, US 2004/0132205, or US 2004/0125424.

An array of beads useful in the invention can also be in a fluid format such as a fluid stream of a flow cytometer or similar device. Exemplary formats that can be used in the invention to distinguish beads in a fluid sample using microfluidic devices are described, for example, in U.S. Pat. No. 6,524,793. Commercially available fluid formats for distinguishing beads include, for example, those used in XMAP™ technologies from Luminex or MPSS™ methods from Lynx Therapeutics.

Any of a variety of arrays known in the art can be used in the present invention. For example, arrays that are useful in the invention can be non-bead-based. A particularly useful array is an Affymetrix™ GeneChip™ array. GeneChip™ arrays can be synthesized in accordance with techniques sometimes referred to as VLSIPS™ (Very Large Scale Immobilized Polymer Synthesis) technologies. Some aspects of VLSIPS™ and other microarray and polymer (including protein) array manufacturing methods and techniques have been described in U.S. Pat. No. 09/536,841, International Publication No. WO 00/58516; U.S. Pat. Nos. 5,143,854, 5,242,974, 5,252, 743, 5,324,633, 5,445,934, 5,744,305, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846, 6,022,963, 6,083,697, 6,291,183, 6,309,831 and 6,428,752; and in PCT Applications Nos. PCT/US99/00730 (International Publication No. WO 99/36760) and PCT/US01/04285, each of which is incorporated herein by reference. Such arrays can hold over 500, 000 probe locations, or features, within a mere 1.28 square centimeters. The resulting probes are typically 25 nucleotides in length. As set forth below in further detail below, a highly efficient synthesis in which substantially all of the probes are full length benefits several embodiments of the invention.

A spotted array can also be used in a method of the invention. An exemplary spotted array is a CodeLink™ Array available from Amersham Biosciences CodeLink™ Activated Slides are coated with a long-chain, hydrophilic polymer containing amine-reactive groups. This polymer is covalently crosslinked to itself and to the surface of the slide. Probe attachment can be accomplished through covalent interaction between the amine-modified 5' end of the oligonucleotide probe and the amine reactive groups present in the polymer. Probes can be attached at discrete locations using spotting pens. Such pens can be used to create features having a spot diameter of, for example, about 140-160 microns. In a preferred embodiment, nucleic acid probes at each spotted feature can be 30 nucleotides long.

Another array that is useful in the invention is one manufactured using inkjet printing methods such as SurePrint™ Technology available from Agilent Technologies. Such methods can be used to synthesize oligonucleotide probes in situ or to attach presynthesized probes having moieties that are reactive with a substrate surface. A printed microarray can contain 22,575 features on a surface having standard slide dimensions (about 1 inch by 3 inches). Typically, the printed probes are 25 or 60 nucleotides in length.

It will be understood that the specific synthetic methods and probe lengths described above for different commercially available arrays are merely exemplary. Similar arrays can be made using modifications of the methods and probes having other lengths such as those set forth elsewhere herein can also be placed at each feature of the array.

Those skilled in the art will know or understand that the composition and geometry of a solid support of the invention can vary depending on the intended use and preferences of the user. Therefore, although microspheres and chips are exemplified herein for illustration, given the teachings and guidance provided herein, those skilled in the art will understand that a wide variety of other solid supports exemplified herein or well known in the art also can be used in the methods and/or compositions of the invention.

Capture probes, for example, can be attached to a solid support of the invention using any of a variety of methods well known in the art. Such methods include for example, attachment by direct chemical synthesis onto the solid support, chemical attachment, photochemical attachment, thermal attachment, enzymatic attachment and/or absorption. These and other methods are will known in the art and applicable for attachment of capture probes in any of a variety of formats and configurations. The resulting probes can be attached to a solid support via a covalent linkage or via non covalent interactions. Exemplary non-covalent interactions are those between a ligand-receptor pair such as streptavidin (or analogs thereof) and biotin (or analogs thereof) or between an antibody and epitope. Once attached to the first solid support, the target sequence, probe or primers are amenable for use in the methods and compositions as described herein.

The invention provides a method of selecting a representational sample of nucleic acid sequences from a complex mixture. The method includes: (a) contacting a complex mixture of nucleic acids under conditions sufficient for hybridization with a population of capture probes complementary to one or more nucleic acids comprising a predetermined portion of the sequence collectively present in said complex mixture to form hybridization complexes of said one or more nucleic acids with said population of probes, said population of capture probes being attached to a solid support, and (b) removing unhybridized nucleic acids to select a representational sample of nucleic acids having a complexity of less than 10% but more than 0.001% of said complex mixture, wherein said representational sample comprises a nucleic acid copy having a proportion of each sequence in the copy relative to all other sequences in the copy substantially the same as the proportions of the sequences in said predetermined portion of one or more nucleic acids within said complex mixture.

The methods of the invention allow for the unbiased selection or isolation of a desired set of nucleic acids from a complex mixture of nucleic acids. Complex mixtures of nucleic acids include, for example, populations that are substantial in size and/or sequence diversity. Particular examples of complex mixtures include, for example, nucleic acids comprising whole genomes, portions of a genome, a chromosome, a portion of a chromosome or one or more particular genomic regions. Particularly useful complex mixtures applicable for selecting a representation sample include, for example, the human genome. Other useful complex mixtures include populations of nucleic acids that include genes, coding regions, exons, introns, mRNA and/or cDNA.

With respect to sequence diversity or sequence complexity, a complex mixture includes a wide range of unique sequence populations. Generally, a complex mixture includes populations having as few as $10^3$ unique sequences and as many as $10^9$ or more. With respect to genomic applications, a complex mixture can range from the number of unique sequences within a small genomic portion up to and including the entire genome. Specific examples of the diversity of a complex mixture that can be employed in the methods of the invention include, for example, $10^3$, $10^4$, $10^5$, $10^6$, $10^7$, $10^8$ or $10^9$ or more. Such populations can be derived from nucleic acids comprising genomes, including human, bacterial and yeast; genomic libraries; cDNA libraries, combinatorial or random libraries and the like.

With respect to the number of sequences, complex mixture size or sequence copy number within a complex mixture, a complex mixture applicable to the methods of the invention also can include a wide range of population sizes. Generally, a complex mixture can include populations having as few as $10^3$ total sequences and as many as $10^{13}$ or more. With respect to genomic applications, a complex mixture can range from the number of total sequences within a small genomic portion up to and including the total number of sequences within the entire genome. Specific examples of the population size of a complex mixture that can be employed in the methods of the invention include, for example, $10^3$, $10^4$, $10^5$, $10^6$, $10^7$, $10^8$, $10^9$, $10^{10}$, $10^{11}$, $10^{12}$ or $10^{13}$ or more total sequences.

Selection of a desired set or representational sample of nucleic acids sequences from a complex mixture allows for the isolation of a subpopulation of nucleic acids which minimizes the sequence bias inherent in other methods of selection. Accordingly, using the methods of the invention a set of nucleic acids can be selected that represent a desired and/or predetermined fraction or complexity of nucleic acids sequences from a complex mixture. For example, the selected sample can represent all, many or some sequences within the complex mixture. Similarly, the selected sample can represent all, many or some unique sequences within the complex mixture. The selected sample also can be generated to represent other nucleic acid sequences within the complex mixture deemed to be informative or useful. For example, the representational sample selected can include, for example, simply a reduction in amount or percentage of sequence information compared to the complex mixture in order to reduce the amount of sequence coverage for a particular region or portion of the complex mixture. Such a selected representational sample can therefore have a complexity of about 0.001, 0.01, 0.1, 1.0, 2.0, 3.0, 4.0, 5.0, 6.0, 7.0, 8.0, 9.0, 10, 15, 20, 25, 30, 35, 40, 45, 50, 55, 60, 65, 70, 75, 80, 85, 90, 95 or 100% compared to the authentic complex mixture or a predetermined portion thereof. Bias and/or distortion of the selected sequence population can be minimized by, for example, minimizing the variance in sequence redundancy, amount or both sequence redundancy and amount.

Representational samples include, for example, subpopulations of the original complex mixture representing a fractional percent and having a substantially similar proportion of sequences compared to the original complex mixture. Fractional percentages are exemplified above in reference to complexity of the authentic complex mixture and can further include, for example, less than about 10%, 1%, 0.1%, 0.01%, 0.001% or less of the complex mixture. The proportional similarity with respect to nucleic acid sequence representation, copy number or both sequence representation and copy number of the representational sample can be, for example, within about 2-, 3-, 4-, 5-, 6-, 7-, 8-, 9-, 10-fold or less compared to the original complex mixture.

Similarly, when compared by statistical analysis indicating, for example, variance or deviation from the original complex mixture, the proportional similarity with respect to nucleic acid sequence representation, copy number or both of the representational sample can be, for example, within about 1, 2, 3, 4, 5, 6, 7, 8, 9, 10, or less standard deviations of the mean compared to the original complex mixture. Given the teachings and guidance provided herein, those skilled in the art will understand that samples other than those exemplified above can have more or less similarity in sequence representation compared to the complex mixture. Such other samples also can be selected using the methods of the invention and still accurately represent sequence or size characteristics of the authentic mixture.

The methods of the invention select for a representational sample from an original complex mixture by hybridization and capture using polynucleotides specific to one or more nucleic acids having a predetermined portion of the sequence within the complex mixture. Briefly, capture probes are contacted with the complex mixture under conditions sufficient for hybridization and the hybridization complexes are separated from unhybridized nucleic acid by washing, for example. The greater the specificity of a capture probe for its complementary sequence within a complex mixture the more accurate the selected representational will be compared to the authentic population.

A variety of hybridization or washing conditions can be used in the selection methods of the invention. Hybridization or washing conditions are well known in the art and can be found described in, for example, Sambrook et al., *Molecular Cloning: A Laboratory Manual, Third Ed.*, Cold Spring Harbor Laboratory, New York (2001) and in Ansubel et al., *Current Protocols in Molecular Biology*, John Wiley and Sons, Baltimore, Md. (1999). Stringency of the hybridization or washing conditions include variations in temperature or buffer composition and can be varied according to the specificity of the reaction needed. A range of stringency includes, for example, high, moderate or low stringency conditions.

Stringent conditions include sequence-dependent specificity and will differ according to length and content of target and probe nucleic acids. Longer sequences hybridize more specifically at higher temperatures. Generally, stringent conditions are selected to be about 5-10° C. lower than the thermal melting point ($T_m$) for the specific sequence at a defined ionic strength and pH. The $T_m$ is the temperature, under defined ionic strength, pH and nucleic acid concentration, at which 50% of the probes complementary to the target hybridize to the target sequence at equilibrium. Differences in the number of hydrogen bonds as a function of base pairing between perfect matches and mismatches can be exploited as a result of their different $T_m$s. Accordingly, a hybrid comprising perfect complementarity will melt at a higher temperature than one comprising at least one mismatch, all other parameters being equal.

Stringent hybridization conditions also include those in which the salt concentration is less than about 1.0 M sodium ion, generally about 0.01 to 1.0 M sodium ion concentration or other salts at pH 7.0 to 8.3 and the temperature is at least about 30° C. for short probes such as 10 to 50 nucleotides and at least about 60° C. for long probes such as greater than 50 nucleotides. Low stringency conditions include NaCl concentrations of about 1.0 M. Furthermore, low stringency conditions can include $MgCl_2$ concentrations of about 10 mM, moderate stringency of about 1-10 mM, and high stringency conditions include concentrations of about 1 mM. Stringent conditions also can be achieved with the addition of helix destabilizing agents such as formamide. For example, low stringency conditions include formamide concentrations of about 0 to 10%, while high stringency conditions utilize formamide concentrations of about 40%. For a further description of hybridization conditions and its relationship to stringency see, for example, Tijssen, *Techniques in Biochemistry and Molecular Biology—Hybridization with Nucleic Acid Probes, Overview of principles of hybridization and the strategy of nucleic acid assays*. (1993).

A population of capture probes employed in the methods of the invention will be selected depending on the desired representational sample to be isolated. As described previously, a representational sample can include, for example, sequences of a whole genome, unique sequences of a genome, genes within a genome, coding regions, exons, intergenic regions, expressed genes, mRNA and the like. A representational sample also can be, for example, a fraction or portion of these nucleic acid categories and/or a fractional percent of the sequence number or diversity of the reference complex mixture. Selection of a representational sample using the methods of the invention entails designing the capture probes representative of, or complementary to, the predetermined population of these sequences and using them as affinity binders to separate the desired sequences from undesired sequences within the complex mixture.

Capture probes to a predetermined portion of nucleic acids within a complex mixture can be designed using nucleic acid sequence information available from a variety of sources and methods well known in the art. For example, nucleic acid sequences, including genomic sequences, can be obtained from any of a variety of sources well known to those skilled in the art. Such sources include for example, user derived, public or private databases, subscription sources and on-line public or private sources. For example, exemplary public databases for obtaining genomic and gene sequences include, for example, dbEST-human, UniGene-human, gb-new-EST, Genbank, Gb_pat, Gb_htgs, Refseq, Derwent Geneseq and Raw Reeds Databases. Access or subscription to these repositories can be found, for example, at the following URL addresses: dbEST-human, gb-new-EST, Genbank, Gb_pat, and Gb_htgs at URL:ftp.ncbi.nih.gov/genbank/; Unigene-human at URL:ftp.ncbi.nih.gov/repository/UniGene/; Refseq at URL:ftp.ncbi.nih.gov/refseq/; Derwent Geneseq at URL:www.derwent.com/geneseq/ and Raw Reads Databases at URL:trace.ensembl.org/. The nucleic acid sequence information additionally can be generated by a user and used directly or stored, for example, in a local database. Various other sources well known to those skilled in the art for genomic, gene and other nucleic acid sequence information also exist and can similarly be used for generating a population of capture probes having a veritable representation of sequences for a predetermined portion of the complex mixture.

The population of capture probes are designed to capture a predetermined portion of the sequence collectively present in one or more nucleic acids within a complex mixture of interest. For example, if the representational sample is desired to include all or substantially all sequences in a genome then a population of capture probe sequences should include probes specific to all or substantially all sequences. Similarly, if a representational sample is desired to include all sequence copies within, for example, one or more chromosomal regions, than a population of capture probe sequences should include probes specific to genome fragments that include all or substantially all sequences within the one or more chromosomal regions. Similarly, populations of capture probes sufficient to form hybridization complexes and select representational samples of, for example, genes, coding regions, exons, introns or a specified percent of the complex mixture can include, for example, capture probes specific to genome fragments that include the predetermined genes, coding regions, exons, introns or having a specified percent of sequence information within the complex mixture.

Accordingly, in certain embodiments, the predetermined portion of the sequence within a complex mixture can include, for example, contiguous or non-contiguous sequences containing the above regions or genomic sequences. The predetermined portion of sequences within a complex mixture also can include, for example, various different sizes of gene fragments containing portions of the above regions or genomic sequences or other genomic sequences. The fragment sizes can vary depending on the design and selection of the capture probes. For example, a predetermined portion of sequences within a complex mixture be contained in genome fragments having sizes of, for example, 25 kilobases (kb), 50 kb, 75 kb, 100 kb, 125 kb, 150 kb, 175 kb, 200 kb, 225 kb, 250 kb, 0.5 megabases (Mb), 0.75 Mb, 1.0 Mb, 2 Mb, 3 Mb, 4 Mb, 5 Mb, 6 Mb, 7 Mb, 8 Mb, 9 Mb, 10 Mb, 20 Mb, 50 Mb, 100 Mb or more. All sizes and range of sizes smaller, larger or in between these exemplary sizes also are included in a predetermined portion that can be targeted for selection of a representational sample.

For representational selection using the methods of the invention, capture probes are attached to a solid support. Generally, attachment occurs, for example, prior to use in the hybridization reaction. Anchorage to a solid support allows for efficient and reproducible selection of predetermined sequences from a complex mixture. Quantitation and reproducibility of selection can be augmented by, for example, standardizing the solid support size, solid support density and capture probe density before, during and/or after capture probe coupling procedures. Capture probe attachment can be performed using any of a variety of methods well known in the art including, for example, chemical, photochemical, photolithography, enzymatic and/or affinity binding.

A wide variety of solid supports or substrates can be employed in the methods of the invention. Exemplary solid supports have been described previously and include, for example, planar structures such as slides, chips, microchips and/or arrays, and particle structures such as magnetic or non-magnetic microspheres.

Capture probes complementary to nucleic acids containing a predetermined portion of the sequence collectively present in one or more nucleic acids within a complex mixture are contacted with the complex mixture under conditions sufficient for hybridization and allowed to form hybridization complexes. Isolation of hybridization complexes can occur by, for example, washing under stringent conditions or separation of the insoluble solid supports having attached hybridization complexes from the soluble unhybridized nucleic acids by centrifugation or sedimentation, for example. The resulting selected nucleic acid population will contain sequences representational of that predetermined portion of sequences present in the original complex mixture. In particular, the resulting selected representational sample can include a nucleic acid copy having a proportion of each sequence in the copy relative to all other sequences in the copy substantially the same as the proportions of sequences in the predetermined portion of one or more nucleic acids within the authentic complex mixture.

Given the teachings and guidance provided herein, those skilled in the art will understand that variations in the methods of the invention also can be employed to further selection of a representational sample from a complex mixture. In particular, any method or method component that can reduce the sequence bias of the selection with respect to sequence diversity and/or population size can be used in combination with the methods of the invention to augment the likeness of the representation sample compared to the authentic complex mixture.

For example, in one specific embodiment variance in the efficiency with which different sequences are present in a captured sample can be reduced by employing relatively long capture probe polynucleotides. A particularly useful length can be, for example, long polynucleotides of at least about 35 nucleotides (nt), generally at least about 40 nt, particularly at least about 45 nt, and more particularly at least about 50 nt or longer. In other specific embodiments, the capture probes are selected to be predominantly full length or selected such that substantially all of the probes are full length, devoid of truncation during polynucleotide synthesis.

Solid surfaces having predominantly full length polynucleotides can be created, for example, by synthesis of the polynucleotides followed by attachment of full length species to the solid surfaces. For example, a polynucleotide can be synthesized in the 3' to 5' direction to include a 5' modified nucleotide moiety and the synthetic product can be subsequently attached to the solid support via the 5' modified nucleotide moiety. Such a method provides the advantage of selecting for the full length polynucleotide because truncated species that typically result from inefficient coupling at any given cycle of the synthesis will not include the 5' modified base and, therefore, will not be capable of attaching to the solid support. It will be understood that, similarly, if a polynucleotide is synthesized in the 5' to 3' direction then attachment to a surface can be carried out via a 3' modified nucleotide moiety. Useful methods for synthesizing polynucleotides are described, for example, in US 60/717,376 entitled "Continuous Polymer Synthesizer" which is incorporated herein by reference. Examples of modified nucleotide moieties useful for attachment of polynulceotides to solid supports include amine, biotin and aldehyde an others described, for example, in US 60/717,376 entitled "Continuous Polymer Synthesizer" which is incorporated herein by reference Another applicable method for synthesizing predominantly full length and/or homogeneous polynucleotide populations includes, for example, synthesizing the capture probe polynucleotides on a solid support with subsequent use of inversion chemistry. In situ inversion of substrate attached nucleic acids can be carried out such that 3' substrate-attached nucleic acids become attach to the substrate at their 5' end and detached at their 3' end. As described above in regard to separating synthesis and attachment steps, attachment via the 5' end selects for full length species and non-full length species produced at-any location on a solid support can be washed away. In situ inversion can be carried out according to methods known in the art such as those described in Kwiatkowski et al., *Nucl. Acids Res.* 27:4710-4714 (1999) and those commercially available as Qt™ OPI Technology from Quiatech AB (Uppsala, Sweden).

Attaching capture probe polynucleotides to solid supports before exposing it to the complex mixture selects for the full-length polynucleotides. In comparison, if polynucleotides are synthesized with a ligand (such as biotin), hybridized to the complex mixture and then captured via the ligand then the representational variance would increase by having any non-full-length polynucleotides compete with the full-length polynucleotides in the hybridization while only capturing the full-length polynucleotides for the selection. In other words, any nucleic acids in the complex mixture that bound to non-full length polynucleotides would be precluded from capture, due to absence of the ligand and would be washed away rather than being represented in the final sample.

In another specific embodiment, reduction in variance in the efficiency with which different sequences are present in a captured sample can be accomplished by, for example, equalizing the Tms of the capture probe polynucleotides. Equalizing or adjusting the Tms within a capture probe population can be accomplished by, for example, varying the length of different polynucleotides in the population, by adding non-complementary bases to the internal and/or terminal portions of certain polynucleotides or by inclusion of bases such as inosine that hybridize to more than one base on the complementary strand. Other methods for equalizing or normalizing Tms between two or more capture probe polynucleotides within a population also can include, for example, synthesizing or engineering insertions, deletions or base substitutions or base modifications that alter the degree of sequence complementarity between probe and predetermined target nucleic acid.

In a further specific embodiment, reduction in variance in the efficiency with which different sequences are present in a captured sample can be accomplished by, for example, use of an excess of capture probe polynucleotides attached to a solid support compared to the predetermined target nucleic acids. Unless otherwise explicitly qualified, excess capture probe or an excess amount of capture probe refers to a molar excess for the complementary nucleic acid portions between capture probe and predetermined target nucleic acid. Use of molar excesses ensures that the capture probe is not a limiting factor and minimizes introduction of variation during the selection procedure. Excess probe amounts will result in a sample being representational with respect to sequence copy number, for example, since substantially all complementary sequences in a complex mixture will form hybridization complexes. To select for a representational sample indicative of unique sequences, for example, modulation of the molar amounts of the capture probe/target ratio can be employed. For example, less than a molar excess can be employed for capture probes complementary to high copy number sequences compared to single copy sequences. The molar ratio of capture probe to target sequence can be modulated in the methods of the invention to achieve essentially desired sequence representation in a selected sample.

In a further specific embodiment, reduction in variance in the efficiency with which different sequences are present in a captured sample can be accomplished by, for example, increasing the efficiency of the capture of the targeted nucleic acid portions of the complex mixture. Capture efficiency can be increased by, for example, designing capture probe polynucleotides to both strands of a complex mixture comprising DNA. Efficiency can be further augmented by, for example, spacing each capture probe within such a pair of capture probes at varying distances along the length of sequence collectively present in a complex mixture of nucleic acid targets, such as the genome sequence collectively present in a population of genomic DNA fragments.

In a further specific embodiment, reduction in variance in the efficiency with which different sequences are present in a captured sample can be accomplished by, for example, increasing the capture efficiency of the complex mixture targets. For example, predetermined portions of nucleic acids within a complex mixture can be reduced to a plurality of smaller sized fragments. Useful fragment sizes furthering hybridization and capture efficiency include, for example, average sizes smaller than at least about 10 kilobases (kb), 9 kb, 8 kb, 7 kb, 6 kb, 5 kb, 4 kb, 3 kb, 2 kb, 1 kb or 0.5 kb or smaller. Particularly useful sizes for fragmenting complex mixture targets include, for example, average sizes between about 5-0.5 kb, 4.5-0.75 kb, 4.0-1.0 kb, 3.5-1.25 kb, 3.0-1.5 kb, 2.5-1.75 kb or about 2.0 kb. Average sizes above, below and between these exemplary ranges also can be employed in the methods of the invention.

Spacing capture probes across the sequences present in predetermined portions of targets within a complex mixture also can be employed to augment efficiency in capture. Spatial separation is particularly useful in connection with fragmentation of the nucleic acids into smaller sizes as described above. For example, optimized capture and selection can be accomplished using average size targets generated from a complex mixture of about 1kb and spatial separation of the population of capture probes about every 1000 nt, 900 nt, 800 nt, 700 nt, 600 nt, 500 nt, 400 nt, 300 nt, or 200 nt or combinations thereof.

Methods for fragmenting nucleic acids are well known in the art. All of such methods are equally applicable in the fragmentation of complex mixtures in preparation for representational selection. Exemplary methods include, for example, enzymatic digestion such as exo- or endonuclease digestion, chemical cleavage, photocleavage and mechanical forces such as sheering and combinations of these methods.

In a further specific embodiment, reduction in variance in the efficiency with which different sequences are present in a captured sample can be accomplished by, for example, attaching single capture probe species to a solid support to generate different populations of supports which each contain a unique capture probe polynucleotide sequence. Manufacturing uniform sequence populations of separate capture probes reduces synthesis variation introduced by differential rates of polynucleotide attachment inherent in the synthesis process. For example, different nucleotides and/or different polynucleotide species compete with each other during the manufacturing process. Such incurred bias can be reduced by separate attachment and subsequent pooling of the various species.

Other exemplary methods of reducing the amount of variance in the population of capture probes attached to solid supports include, for example, the use of similar amounts of starting solid supports, minimizing or eliminating sampling from the in-process reactions and/or complete or nearly complete extraction of the solid supports into the final population pool. Similar amounts of starting solid supports can be determined by, for example, normalizing the weight, volume or count. Another useful method for creating a narrow distribution of capture probe populations attached to solid supports and/or the total size, mass or number of solid supports can include, for example, the use of a patterned substrate that can select the size of solid support particles such as microspheres, for example, an exemplary patterned substrate is the etched substrate used in connection with BeadArray™ technology (Illumina, Inc., San Diego, Calif.). Additionally, the complexity of the microsphere pool can be varied depending upon the complexity of the predetermined nucleic acid portion of the complex mixture of interest.

In a further specific embodiment, reduction in variance in the efficiency with which different sequences are present in a captured sample can be accomplished by, for example, using solid supports such as microspheres having different properties which allow further selection of the complex mixture nucleic acid targets while purposefully avoiding problematic nucleic acid portions or sequences. For example, some sequences such as repeated sequences are overly represented in gDNA. Because these sequences are present in high concentration relative to non-repeated sequences, they contribute disproportionally to non-specific binding during hybridization. Non-specific binding increases the variance in a selected sample, thereby compromising representation of the sample. To reduce or eliminate such repeated sequences, for example, and make them less available to contribute to non-specific binding, capture probes for such undesirable sequences can be designed and employed in a preparatory step to cure the complex mixture of some, many or substantially all of such unwanted sequences.

For example, in this specific embodiment, different solid support-attached capture probe populations can be used for a selection step compared to those populations used for representational selection of complex mixture target nucleic acids. The preparatory step to reduce undesirable sequences can be employed, for example, prior to, or simultaneous with, a selection step for isolation of a desired representational sample. Solid support properties allowing removal or separation of undesirable sequences simultaneously with selection of a representational sample include, for example, differential size, differential mass, shape or magnetism. For example, paramagnetic microspheres can be attached to capture probes specific for a complex mixture's target nucleic acids and non-magnetic microspheres used for the capture probes specific to undesirable sequences. Separation of the paramagnetic microspheres with a magnetic force will result in separation of the two classes of a complex mixture's nucleic acids. Given the teachings and guidance provided herein, this application also is equally applicable selection of a complex mixture's target nucleotide sequences in a stepwise fashion as described above, for example. Stepwise selection also can be employed, for example, by using capture probes with different Tms. For example, by selecting a subpopulation using capture probes having a first Tm and subsequently selecting a further subpopulation using capture probes having a second Tm. Other properties of the solid support also can be useful in this exemplified embodiment.

In a further specific embodiment, reduction in variance in the efficiency with which different sequences are present in a captured sample can be accomplished by, for example, increasing hybridization specificity of the capture probe to reduce non-specific binding through use of, for example, stringent hybridization conditions. As exemplified previously, a wide variety of methods are well known in the art for increasing the hybridization stringency and, therefore, the specificity of hybridization complex formation. Such methods include, for example, modulating the temperature, ionic salts, non-ionic compounds (e.g. formamide) and/or pH. Additionally, procedures such as cyclic or gradient temperature annealing also can be employed, which is particularly useful when the complex mixture's target nucleic acid or nucleic acids are present in limiting concentration. Furthermore, stringent washes can additionally be performed to further reduce non-specific binding. Such washes can include, for example, high-temperature wash(es), high salt concentration, high non-ionic compounds and the like.

In a further specific embodiment, reduction in variance in the efficiency with which different sequences are present in a captured sample can be accomplished by, for example, separating the capture probe-containing solid support hybridization complexes from the complex mixture- -containing unhybridized nucleic acids. This separation can be facilitated by, for example, gravity, centrifugation or by magnetism (if paramagnetic solid support are used), followed by liquid or solid support removal.

In a further specific embodiment, reduction in variance in the efficiency with which different sequences are present in a captured sample can be accomplished by, for example, eluting a bound complex mixture or a predetermined nucleic acid portion thereof nearly completely from the solid supports. This elution step can be accomplished by, for example, use of very high stringency conditions, including high temperatures.

In yet a further specific embodiment, reduction in variance in the efficiency with which different sequences are present in a captured sample can be accomplished by, for example, quantifying the on-chip pull-out and using the value to normalize analysis results. Any method known in the art for quantifying sequences can be used including, for example, molecular beacon technology.

Therefore, the invention provides a nucleic acid population comprising a representational sample having a specified complexity of a complex mixture. The specified complexity can be, for example, less than 10% but more than 0.001% of a complex mixture. The representational sample includes a nucleic acid copy having a proportion of each sequence in the copy relative to all other sequences in the copy substantially the same as the proportions of sequences in a predetermined portion of a sequence collectively present in one or more nucleic acids within the complex mixture. The representational sample also can be attached to a solid support.

The invention also provides a method wherein a representational sample of the invention selected from a complex mixture of nucleic acids is further used in subsequent procedure or analysis. The subsequent analysis step can be any qualitative, quantitative or analytical method employed with nucleic acids known to those skilled in the art. Particularly useful methods include a subsequent step selected from, for example, amplification, sequencing, targeted resequencing, nucleic acid detection, copy number analysis, gene expression analysis, genotyping, determination of copy number, determination of loss of heterozygosity, methylation analysis or nucleotide detection. All of such nucleic acid analysis procedures also are particularly useful in, for example, medical diagnosis and/or prognosis, including personalized medical diagnosis and/or prognosis procedures.

Exemplary embodiments of these various subsequent analysis procedures are set forth below for purposes of illustration. These exemplary procedures are well known in the art and are equally applicable for use in conjunction with a representational sample of the invention. Similarly, these and/or other well known procedures also can be combined in various formats and configurations to achieve essentially any desired analysis of a representational sample of the invention. Given the teachings and guidance provided herein, those skilled in the art will understand that the representational samples of the invention can be employed in a variety of different procedures to obtain a sought after result. Similarly, a representational sample of the invention also can be employed in such subsequent analysis procedures in formats or configurations that include, for example, solution phase procedures, solid phase procedures and/or array or chip-type formats. All of such procedures and formats for nucleic acid detection or analysis are well known to those skilled in the art and can be found described in, for example, WO 2005/003304 A2 and in U.S. Patent Application Publications 20050181394, 20050059048, 20050053980, 20050037393, 20040259106, 20040259100.

One particularly useful subsequent analysis of a representational sample of the invention includes, for example, nucleotide sequence characterization or sequence analysis. With the ability to select a representational sample from a complex mixture such as a genome or portion of a genome, accurate sequencing analysis can be efficiently performed. Methods for manual or automated sequencing are well known in the art and include, but are not limited to, Sanger sequencing, pyrosequencing, sequencing by hybridization, sequencing by ligation and the like. Sequencing methods can be preformed manually or using automated methods. Furthermore, the methods set forth herein can be used to prepare nucleic acids for sequencing using commercially available methods such as automated Sanger sequencing (available from Applied Biosystems, Foster City Calif.) or pyrosequencing (available from 454 Lifesciences, Branford, Conn. and Roche Diagnostics, Basel, Switzerland).

A nucleic acid sample obtained using methods described herein can be amplified prior to sequence analysis. A particularly useful method is emulsion PCR. However, amplification need not be carried out if the sample provides sufficient quantity to suit the particular method being used. A nucleic acid sample to be sequenced can be attached to a solid phase using methods and substrates described elsewhere herein or otherwise known in the art. The sample will typically be attached as a population of separate nucleic acids, such as those encoding genome fragments, that can be distinguished from each other. Microarrays are particularly useful for sequence analysis.

A population of nucleic acids can be sequenced using methods in which a primer is hybridized to each nucleic acid such that the nucleic acids form templates and modification of the primer occurs in a template directed fashion. The modification can be detected to determine the sequence of the template. For example, the primers can be modified by extension using a polymerase and extension of the primers can be monitored under conditions that allow the identity and location of particular nucleotides to be determined. For example, extension can be monitored and sequence of the template nucleic acids determined using pyrosequencing which is described in further detail below, in US 2005/0130173; US 2006/0134633; U.S. Pat. Nos. 4,971,903; 6,258,568 and 6,210,891, each of which is incorporated herein by reference and is also commercially available, see above. Extension can also be monitored according to addition of labeled nucleotide analogs by a polymerase, using methods described, for example, elsewhere herein and in U.S. Pat. Nos. 4,863,849; 5,302,509; 5,763,594; 5,798,210; 6,001,566; 6,664,079; US 2005/0037398; and U.S. Pat. No. 7,057,026, each of which is incorporated herein by reference. Polymerases useful in sequencing methods are typically polymerase enzymes derived from natural sources. It will be understood that polymerases can be modified to alter their specificity for modified nucleotides as described, for example, in WO/ 01/23411; U.S. Pat. No. 5,939,292; and WO 05/024010, each of which is incorporated herein by reference. Furthermore, polymerases need not be derived from biological systems.

A further modification of primers that can be used to determine the sequence of templates to which they are hybridized is ligation. Such methods are referred to as sequencing by ligation and are described, for example, in Shendure et al. Science 309:1728-1732 (2005); U.S. Pat. Nos. 5,599,675; and 5,750,341, each of which is incorporated herein by reference. It will be understood that primers need not be modified in order to determine the sequence of the template to which they are attached. For example, sequences of template nucleic acids can be determined using methods of sequencing by hybridization such as those described in U.S. Pat. Nos. 6,090,549; 6,401,267 and 6,620,584.

Another particularly useful subsequent analysis of a representational sample of the invention includes, for example, targeted resequencing of nucleic acid samples. This analysis is particularly useful in human genomics, for example, because it increases the accuracy of the original sequence determination. The analysis consists of at least a second sequence determination of a desired read sequence. A representational sample of the invention can be employed in connection with this procedure because a nucleic acid portion targeted for resequencing can be efficiently selected from a complex mixture using the methods of the invention.

Similarly, a representational sample of the invention also can be employed in subsequent analyses that include gene and/or sequence copy number analysis for a variety of applications in human genomic medicine. Because representational samples of the invention can be generated to represent a true replica of a complex mixture these selected nucleic acid populations of the invention can be efficiently used for quantitation of gene copy number. Any of the various nucleic acid detection formats exemplified further below or well known in the art can be used for quantifying the amount of a gene or other sequence in representational sample. The amount or copy number determined to be present in a representational sample will be indicative of the amount or copy number of the assayed sequence or sequences in the authentic complex mixture.

A further subsequent analysis that a representational sample of the invention can be usefully employed with includes, for example, gene expression analysis. In particular, methods for on-array labeling of probe nucleic acids using primer extension methods can be used in the detection of RNA or cDNA for such expressed sequence determinations. Probe-cDNA hybrids can be detected by polymerase-based primer extension methods as exemplified herein and known in the art. Alternatively, for array-hybridized mRNA, reverse-transcriptase-based primer extension can be employed. There are several particularly useful attributes of on-array labeling for gene expression analysis. Labeling costs can be dramatically decreased since the amounts of labeled nucleotides employed are substantially less compared to methods for labeling captured targets. Secondly, cross-hybridization can be reduced since a target must both hybridize and also contain perfect complementarity at its 3' terminus for label incorporation in a primer extension reaction. Similarly, OLA or primer extension and ligation methods as described further below can be used for detection of hybridized cDNA or mRNA. The latter two methods typically employ the addition of an exogenous nucleic acid for each sequence queried. However, such methods can be useful in applications where the use of primer extension leads to unacceptable levels of ectopic extension.

The above described on-array labeling with primer extension also can be used to monitor alternate splice sites of nucleic acids within a selected representational sample by, for example, designing the 3' probe terminus to coincide with a splice junction of a target cDNA or mRNA. The terminus can be placed to uniquely identify all the relevant possible acceptor splice sites for a particular gene. For example, the first 45 bases can be chosen to lie entirely within the donor exon, and the last 5 3'-bases can lie in a set of possible splice acceptor exons that become spliced adjacent to the first 45 bases. The above exemplary gene expression analysis methods can be found describe in, for example, WO 2005/003304 A2, and in U.S. Patent Application Publications 20050181394, 20050059048, 20050053980, 20050037393, 20040259106, 20040259100. Given the teachings and guidance provided herein, these and other expression analysis methods can be beneficially employed in the analysis of gene expression indicative of a pathological condition using a representational sample of the invention.

Still further useful subsequent analyses of a representational sample can include a wide variety of nucleic acid detection, including nucleotide detection methods. As with the above exemplary applications of a representational sample of the invention, measurements of genetic markers, mutations and the like using an accurate replica of a complex mixture such as a genome yields more accurate and reproducible results and, therefore, more precise disease correlations and diagnostic determinations.

Any of the subsequent analyses exemplified herein can be used in combination with any other analyses or with another method well known in the art. Such subsequent analyses, or combinations thereof, also can be performed with or without nucleic acid amplification methods. Exemplary nucleic acid detection, nucleotide detection and amplification procedures are described further below.

In a particular nucleic acid detection embodiment, arrayed nucleic acid probes can be modified while hybridized to a representational sample for detection. Such embodiments, include, for example, those utilizing ASPE (Allele Specific Primer Extension), SBE (Single Base Extension), oligonucleotide ligation amplification (OLA), extension ligation, invader technology, probe cleavage or pyrosequencing as described in U.S. Pat. No. 6,355,431 B1, U.S. Ser. No. 10/177,727 and/or below. Thus, subsequent analyses steps of the invention can be carried out in a mode wherein an immobilized probe is modified instead of a representational sample nucleic acid captured by a probe. Alternatively, detection can include modification of the representational sample nucleic acids while hybridized to probes. Exemplary modifications include those that are catalyzed by an enzyme such as a polymerase.

Extension assays are useful for nucleic acid and/or nucleotide detection. Extension assays are generally carried out by modifying the 3' end of a first nucleic acid when hybridized to a second nucleic acid. The second nucleic acid can act as a template directing the type of modification, for example, by base pairing interactions that occur during polymerase-based extension of the first nucleic acid to incorporate one or more nucleotide. Polymerase extension assays are particularly useful, for example, due to the relative high-fidelity of polymerases and their relative ease of implementation. Extension assays can be carried out to modify nucleic acid probes that have free 3' ends, for example, when bound to a substrate such as an array. Exemplary approaches that can be used include, for example, allele-specific primer extension (ASPE), single base extension (SBE), or pyrosequencing.

In particular embodiments, single base extension (SBE) can be used for nucleic acid or nucleotide detection. Briefly, SBE utilizes an extension probe that hybridizes to a target representational sample nucleic acid at a location that is proximal or adjacent to a detection position, the detection position being indicative of a particular sequence. A polymerase can be used to extend the 3' end of the probe with a nucleotide analog labeled with a detection label. Based on the fidelity of the enzyme, a nucleotide is only incorporated into the extension probe if it is complementary to the detection position in the target representational sample nucleic acid. If desired, the nucleotide can be derivatized such that no further extensions can occur, and thus only a single nucleotide is added. The presence of the labeled nucleotide in the extended probe can be detected for example, at a particular location in an array and the added nucleotide identified to determine the identity of the analyte sequence. SBE can be carried out under known conditions such as those described in U.S. patent application Ser. No. 09/425,633. A labeled nucleotide can be detected using methods such as those set forth above or described elsewhere such as Syvanen et al., *Genomics* 8:684-692 (1990); Syvanen et al., *Human Mutation* 3:172-179 (1994); U.S. Pat. Nos. 5,846,710 and 5,888,819; Pastinen et al., *Genomics Res.* 7(6):606-614 (1997).

As will be appreciated by those in the art, the configuration of an SBE reaction can take on any of several forms. In particular embodiments, the reaction can be done in solution, and then the newly synthesized strands, with the base-specific detectable labels, can be detected. For example, they can be directly hybridized to capture probes that are complementary to the extension primers, and the presence of the label can then be detected. Such a configuration is useful, for example, when representational sample nucleic acids are arrayed as capture probes. Alternatively, the SBE reaction can occur on a surface. For example, a representational sample nucleic acid can be captured using a first capture probe that hybridizes to a first target domain of the fragment, and the reaction can proceed such that the probe is modified as described above.

Single base sequencing (SBS) is an extension assay that can be carried out as set forth above for SBE with the exception that one or more non-chain terminating nucleotides are included in the extension reaction. Thus, in accordance with the invention, one or more non-chain terminating nucleotides can be included in an SBE reaction including, for example, those exemplified above.

ASPE is an extension assay that utilizes extension probes that differ in nucleotide composition at their 3' end. Briefly, ASPE can be carried out by hybridizing a target representational sample nucleic acid to an extension probe having a 3' sequence portion that is complementary to a detection position and a 5' portion that is complementary to a sequence that is adjacent to the detection position. Template directed modification of the 3' portion of the probe, for example, by addition of a labeled nucleotide by a polymerase yields a labeled extension product, but only if the template includes the target sequence. The presence of such a labeled primer-extension product can then be detected, for example, based on its location in an array to indicate the presence of a particular analyte sequence.

In particular embodiments, ASPE can be carried out with multiple extension probes that have similar 5' ends such that they anneal adjacent to the same detection position in a target representational sample nucleic acid but different 3' ends, such that only probes having a 3' end that complements the detection position are modified by a polymerase. For example, a probe having a 3' terminal base that is complementary to a particular detection position is referred to as a perfect match (PM) probe for the position, whereas probes that have a 3' terminal mismatch base and are not capable of being extended in an ASPE reaction are mismatch (MM) probes for the position. The presence of the labeled nucleotide in the PM probe can be detected and the 3' sequence of the probe determined to identify a particular analyte sequence. An ASPE reaction can include 1, 2, or 3 different MM probes, for example, at discrete array locations, the number being chosen depending upon the diversity occurring at the particular locus being assayed. For example, two probes can be used to determine which of 2 alleles for a particular locus are present in a sample, whereas three different probes can be used to distinguish the alleles of a 3-allele locus. In particular embodiments, an ASPE reaction can include a nucleotide analog that is derivatized to be chain terminating. Thus, a PM probe in a probe-fragment hybrid can be modified to incorporate a single nucleotide analog without further extension.

Pyrosequencing is an extension assay that can be used to add one or more nucleotides to a detection position(s); it is similar to SBE except that identification of an analyte sequence is based on detection of a reaction product, pyrophosphate (PPi), produced during the addition of a dNTP to an extended probe, rather than on a label attached to the nucleotide. One molecule of PPi is produced per dNTP added to the extension primer. That is, by running sequential reactions with each of the nucleotides, and monitoring the reaction products, the identity of the added base is determined. Pyrosequencing can be used in the invention using conditions such as those described in US 2002/0001801.

In particular embodiments, modification of immobilized probe-representational sample nucleic acid hybrids can include cleavage or degradation of hybrids having one or more mismatched base pair. As with other modifications set forth herein, conditions can be employed that result in selective modification of hybrids having one or more mismatch compared to perfectly matched hybrids. Exemplary agents include enzymes that recognize and cleave hybrids having mismatched base pairs such as a DNA glycosylase, Cel I, T4 endonuclease VII, T7 endonuclease I, mung bean endonuclease or Mut-y or others such as those described in Bradley et al., *Nucl. Acids Res.* 32:2632-2641 (2004). Cleavage products produced from mismatched hybrids can be removed, for example, by washing. Accordingly, a subsequent analysis method of the invention can include modifying immobilized probe-representational sample nucleic acid hybrids using ASPE along with cleavage of mismatch hybrids. In another particular embodiment, an ASPE reaction can be carried out under conditions in which extension of perfect match probe-representational sample nucleic acid hybrids is driven to completion and substantial amounts of mismatch probe-fragment hybrids are also extended.

If desired, an immobilized probe that is not part of a probe-fragment hybrid can be selectively modified compared to a probe-representational sample nucleic acid hybrid. Selective modification of non-hybridized probes can be used to increase assay specificity and sensitivity, for example, by removing probes that are labeled in a template independent manner during the course of a polymerase extension assay. A particularly useful selective modification is degradation or cleavage of single stranded probes that are present in a population or array of probes following contact with target fragments under hybridization conditions. Exemplary enzymes that degrade single stranded nucleic acids include, without limitation, Exonuclease I or lambda Exonuclease.

In embodiments utilizing probes with reactive hydroxyls at their 3' ends and polymerase extension, a useful exonuclease is one that preferentially digests single stranded DNA in the 3' to 5' detection. Thus, double stranded probe-target hybrids that form under particular assay conditions are preferentially protected from degradation as is the 3' overhang of the target that serves as a template for polymerase extension of the probe. However, single stranded probes not hybridized to target under the assay conditions are preferentially degraded. Furthermore, such exonuclease treatment can preferentially degrade single stranded regions of representational sample nucleic acids or other nucleic acids in cases where the fragments or nucleic acids are retained by an array due to interaction with non-probe interacting portions of target nucleic acids. Thus, exonuclease treatment can prevent artifacts that may arise due to a bridged network of 2 or more nucleic acids bound to a probe. Digestion with exonuclease is typically carried out after a probe extension step.

In some embodiments, detection of analyte sequences from a representational sample can include amplification of representational sample nucleic acid targets following formation of proberepresentational sample nucleic acid hybrids, resulting in a significant increase in the number of target molecules. Target amplification-based detection techniques can include, for example, the polymerase chain reaction (PCR), strand displacement amplification (SDA), or nucleic acid sequence based amplification (NASBA). A particularly useful amplification method is emulsion PCR. Emulsion PCR methods are known in the art and, briefly, involve emulsifying a population of nucleic acids with amplification reagents in a water-oil mixture under conditions in which, on average, individual nucleic acids are captured in separate compartments. The methods provide the advantage of capturing and amplifying unique nucleic acids in each compartment. Typically, each nucleic acid is attached to a bead in the compartments and the bead can be subsequently manipulated to keep sequences separated, for example, by attachment to identifiable locations on an array substrate. Emulsion PCR can be carried out as described, for example, in US 2005/0042648; US 2005/0079510; US 2005/0064460; US 2005/0227264; and WO 05/010145, each of which is incorporated herein by reference. A representative sample obtained using a method described herein can be amplified using emulsion PCR and, if desired, the amplicons can be sequenced or otherwise analyzed using the methods set forth herein.

Alternatively, rather than amplify the target, alternate techniques can use the target as a template to replicate a hybridized probe, allowing a small number of target molecules to result in a large number of signaling probes, that then can be detected. Probe amplification-based strategies include, for example, the ligase chain reaction (LCR), cycling probe technology (CPT), invasive cleavage techniques such as Invader™ technology, Q-Beta replicase (QβR) technology or sandwich assays. Such techniques can be carried out, for example, under conditions described in U.S. Ser. No. 60/161, 148, 09/553,993 and 090/556,463; and U.S. Pat. No. 6,355, 431 B1, or as set forth below. These techniques are exemplified below, in the context of representational sample nucleic acids used as target nucleic acids that are hybridized to arrayed nucleic acid probes. It will be understood that in such embodiments representational sample nucleic acid can be arrayed as probes and hybridized to synthetic nucleic acid targets.

Detection with oligonucleotide ligation amplification (OLA) involves the template-dependent ligation of two smaller probes into a single long probe, using a representational sample nucleic acid target sequence as the template. In a particular embodiment, a single-stranded target sequence includes a first target domain and a second target domain, which are adjacent and contiguous. A first OLA probe and a second OLA probe can be hybridized to complementary sequences of the respective target domains. The two OLA probes are then covalently attached to each other to form a modified probe. In embodiments where the probes hybridize directly adjacent to each other, covalent linkage can occur via a ligase. In one embodiment one of the ligation probes may be attached to a surface such as an array or a particle. In another embodiment both ligation probes may be attached to a surface such as an array or a particle.

Alternatively, an extension ligation assay can be used wherein hybridized probes are non-contiguous and one or more nucleotides are added along with one or more agents that join the probes via the added nucleotides. Exemplary agents include, for example, polymerases and ligases. If desired, hybrids between modified probes and targets can be denatured, and the process repeated for amplification leading to generation of a pool of ligated probes. As above, these extension-ligation probes can be but need not be attached to a surface such as an array or a particle. Further conditions for extension ligation assay that are useful in the invention are described, for example, in U.S. Pat. No. 6,355,431 B1 and U.S. application Ser. No. 10/177,727.

A modification of OLA is referred to as the ligation chain reaction (LCR) when double-stranded representational sample nucleic acid targets are used. In LCR, the target sequence can be denatured, and two sets of probes added: one set as outlined above for one strand of the target, and a separate set (i.e. third and fourth primer probe nucleic acids) for the other strand of the target. Conditions can be used in which the first and second probes hybridize to the target and are modified to form an extended probe. Following denaturation of the target-modified probe hybrid, the modified probe can be used as a template, in addition to the second target sequence, for the attachment of the third and fourth probes. Similarly, the ligated third and fourth probes can serve as a template for the attachment of the first and second probes, in addition to the first target strand. In this way, an exponential, rather than just a linear, amplification can occur when the process of denaturation and ligation is repeated.

The modified OLA probe product can be detected in any of a variety of ways. In a particular embodiment, a template-directed probe modification reaction can be carried out in solution and the modified probe hybridized to a capture probe in an array. A capture probe is generally complementary to at least a portion of the modified OLA probe. In an exemplary embodiment, the first OLA probe can include a detectable label and the second OLA probe can be substantially complementary to the capture probe. A non-limiting advantage of this embodiment is that artifacts due to the presence of labeled probes that are not modified in the assay are minimized because the unmodified probes do not include the complementary sequence that is hybridized by the capture probe. An OLA detection technique can also include a step of removing unmodified labeled probes from a reaction mixture prior to contacting the reaction mixture with a capture probe as described for example in U.S. Pat. No. 6,355,431 B1.

Alternatively, a representational sample nucleic acid target can be immobilized on a solid-phase surface and a reaction to modify hybridized OLA probes performed on the solid phase surface. Unmodified probes can be removed by washing under appropriate stringency. The modified probes can then be eluted from the representational sample nucleic acid target using denaturing conditions, such as, 0.1 N NaOH, and detected as described herein. Other conditions in which a representational sample nucleic acid can be detected when used as a target sequence in an OLA technique include, for example, those described in U.S. Pat. Nos. 6,355,431 B1, 5,185,243, 5,679,524 and 5,573,907; EP 0 320 308 B1; EP 0 336 731 B1; EP 0 439 182 B1; WO 90/01069; WO 89/12696; WO 97/31256; and WO 89/09835, and U.S. Ser. Nos. 60/078,102 and 60/073,011.

Analyte sequences can be detected in a subsequent analysis method of the invention using rolling circle amplification (RCA). In a first embodiment, a single probe can be hybridized to a representational sample nucleic acid target such that the probe is circularized while hybridized to the target. Each terminus of the probe hybridizes adjacently on the target nucleic acid and addition of a polymerase results in extension of the circular probe. However, since the probe has no terminus, the polymerase continues to extend the probe repeatedly. This results in amplification of the circular probe. Following RCA the amplified circular probe can be detected. This can be accomplished in a variety of ways; for example, the primer can be labeled or the polymerase can incorporate labeled nucleotides and labeled product detected by a capture probe in a detection array. Rolling-circle amplification can be carried out under conditions such as those generally described in Baner et al. (1998) *Nuc. Acids Res.* 26:5073-5078; Barany, F. (1991) *Proc. Natl. Acad. Sci. USA* 88:189-193; and Lizardi et al. (1998) *Nat Genet.* 19:225-232.

Furthermore, rolling circle probes used in the invention can have structural features that render them unable to be replicated when not annealed to a target. For example, one or both of the termini that anneal to the target can have a sequence that forms an intramolecular stem structure, such as a hairpin structure. The stem structure can be made of a sequence that allows the open circle probe to be circularized when hybridized to a legitimate target sequence but results in inactivation of uncircularized open circle probes. This inactivation reduces or eliminates the ability of the open circle probe to prime synthesis of a modified probe in a detection assay or to serve as a template for rolling circle amplification. Exemplary probes capable of forming intramolecular stem structures and methods for their use which can be used in the invention are described in U.S. Pat. No. 6,573,051.

In another embodiment, detection can include OLA followed by RCA. In this embodiment, an immobilized primer can be contacted with a representational sample nucleic acid target. Complementary sequences will hybridize with each other resulting in an immobilized duplex. A second primer can also be contacted with the target nucleic acid. The second primer hybridizes to the target nucleic acid adjacent to the first primer. An OLA reaction can be carried out to attach the first and second primer as a modified primer product, for example, as described above. The representational sample nucleic acid can then be removed and the immobilized modified primer product, hybridized with an RCA probe that is complementary to the modified primer product but not the unmodified immobilized primer. An RCA reaction can then be performed.

In a particular embodiment, a padlock probe can be used both for OLA and as the circular template for RCA. Each terminus of the padlock probe can contain a sequence complementary to a representational sample nucleic acid target. More specifically, the first end of the padlock probe can be substantially complementary to a first target domain, and the second end of the RCA probe can be substantially complementary to a second target domain, adjacent to the first domain. Hybridization of the padlock probe to the representational sample nucleic acid target results in the formation of a hybridization complex. Ligation of the discrete ends of a single oligonucleotide results in the formation of a modified hybridization complex containing a circular probe that acts as an RCA template complex. Addition of a polymerase to the RCA template complex can allow formation of an amplified product nucleic acid. Following RCA, the amplified product nucleic acid can be detected, for example, by hybridization to an array either directly or indirectly and an associated label detected.

A padlock probe used in the invention can further include other characteristics such as an adaptor sequence, restriction site for cleaving concatamers, a label sequence or a priming site for priming the RCA reaction as described, for example, in U.S. Pat. No. 6,355,431 B1. This same patent also describes padlock probe methods that can be used to detect analyte sequence of representational sample nucleic acid targets in a method of the invention.

A variation of LCR that can be used to detect an analyte sequence in a subsequent analysis method of the invention utilizes chemical ligation under conditions such as those described in U.S. Pat. Nos. 5,616,464 and 5,767,259. In this embodiment, similar to enzymatic modification, a pair of probes can be utilized, wherein the first probe is substantially complementary to a first domain of a target representational sample nucleic acid and the second probe is substantially complementary to an adjacent second domain of the target. Each probe can include a portion that acts as a "side chain" that forms one half of a non-covalent stem structure between the probes rather than binding the target sequence. Particular embodiments utilize substantially complementary nucleic acids as the side chains. Thus, upon hybridization of the probes to the target sequence, the side chains of the probes are brought into spatial proximity. At least one of the side chains can include an activatable cross-linking agent, generally covalently attached to the side chain, that upon activation, results in a chemical cross-link or chemical ligation with the adjacent probe. The activatable group can include any moiety that will allow cross-linking of the side chains, and include groups activated chemically, photonically or thermally, such as photoactivatable groups. In some embodiments a single activatable group on one of the side chains is enough to result in cross-linking via interaction to a functional group on the other side chain; in alternate embodiments, activatable groups can be included on each side chain. One or both of the probes can be labeled Once a hybridization complex is formed, and the cross-linking agent has been activated such that the probes have been covalently attached to each other, the reaction can be subjected to conditions to allow for the disassociation of the hybridization complex, thus freeing up the target to serve as a template for the next ligation or cross-linking. In this way, signal amplification can occur, and the cross-linked products can be detected, for example, by hybridization to an array either directly or indirectly and an associated label detected.

In particular embodiments, amplification-based detection can be achieved using invasive cleavage technology. Using such an approach, a representational sample nucleic acid target can be hybridized to two distinct probes. The two probes are an invader probe, which is substantially complementary to a first portion of the representational sample nucleic acid target, and a signal probe, which has a 3' end substantially complementary to a sequence having a detection position and a 5' non-complementary end which can form a single-stranded tail. The tail can include a detection sequence and typically also contains at least one detectable label. However, since a detection sequence in a signal probe can function as a target sequence for a capture probe, sandwich configurations utilizing label probes can be used as described herein and the signal probe need not include a detectable label.

Hybridization of the invader and signal probes near or adjacent to one another on a representational sample nucleic acid target can form any of several structures useful for detection of the probe-fragment hybrid. For example, a forked cleavage structure can form, thereby providing a substrate for a nuclease which cleaves the detection sequence from the signal probe. The site of cleavage is controlled by the distance or overlap between the 3' end of the invader probe and the downstream fork of the signal probe. Therefore neither oligonucleotide is cleaved when misaligned or when unattached to a representational sample nucleic acid target.

In particular embodiments, a thermostable nuclease that recognizes the forked cleavage structure and catalyzes release of the tail can be used, thereby allowing thermal cycling of the cleavage reaction and amplified, if desired. Exemplary nucleases that can be used include, without limitation, those derived from *Thermus aquaticus, Thermus flavus*, or *Thermus thermophilus*; those described in U.S. Pat. Nos. 5,719,028 and 5,843,669, or Flap endonucleases (FENs) as described, for example, in U.S. Pat. No. 5,843,669 and Lyamichev et al., *Nature Biotechnology* 17:292-297 (1999).

If desired, the 3' portion of a cleaved signal probe can be extracted, for example, by binding to a solid-phase capture tag such as bead bound streptavidin, or by crosslinking through a capture tag to produce aggregates. The 5' detection sequence of a signal probe, can be detected using methods set forth below such as hybridization to a probe on an array. Invasive cleavage technology can further be used in the invention using conditions and detection methods described, for example, in U.S. Pat. Nos. 6,355,431; 5,846,717; 5,614,402; 5,719,028; 5,541,311; or 5,843,669.

A further amplification-based detection technique that can be used to detect an analyte sequence is cycling probe technology (CPT). A CPT probe can include two probe sequences separated by a scissile linkage. The CPT probe is substantially complementary to a representational sample nucleic acid target sequence and thus will hybridize to it to form a probe-fragment hybrid. The CPT probe can be hybridized to a representational sample nucleic acid target in a method of the invention. Typically the temperature and probe sequence are selected such that the primary probe will bind and shorter cleaved portions of the primary probe will dissociate. Depending upon the particular application, CPT can be done in solution, or either the target or scissile probe can be attached to a solid support. A probe-fragment hybrid formed in the methods can be subjected to cleavage conditions which cause the scissile linkage to be selectively cleaved, without cleaving the target sequence, thereby separating the two probe sequences. The two probe sequences can then be disassociated from the target. In particular embodiments, excess probe can be used and the reaction allowed to be repeated any number of times such that the effective amount of cleaved probe is amplified.

Any linkage within a CPT probe that can be selectively cleaved when the probe is part of a hybridization complex, that is, when a double-stranded complex is formed can be used as a scissile linkage. Any of a variety of scissile linkages can be used in the invention including, for example, RNA which can be cleaved when in a DNA:RNA hybrid by various double-stranded nucleases such as ribonucleases. Such nucleases will selectively nick or excise RNA nucleosides from a RNA:DNA hybridization complex rather than DNA in such a hybrid or single stranded DNA. Further examples of scissile linkages and cleaving agents that can be used in the invention are described in U.S. Pat. No. 6,355,431 B1 and references cited therein.

Upon completion of a CPT cleavage reaction, the uncleaved scissile probes can be removed or neutralized prior to detection of cleaved probes to avoid false positive signals, if desired. This can be done in any of a variety of ways including, for example, attachment of the probes to a solid support prior to cleavage such that following the CPT reaction, cleaved probes that have been released into solution can be physically separated from uncleaved probes remaining on the support. Uncleaved and cleaved probes can also be separated based on differences in length, capture of a particular binding label or sequence using, for example, methods described in U.S. Pat. No. 6,355,431.

Cleaved probes produced by a CPT reaction can be detected using methods such as hybridization to an array or other methods set forth herein. For example, a cleaved probe can be bound to a capture probe, either directly or indirectly, and an associated label detected.

CPT technology can be carried out under conditions described, for example, in U.S. Pat. Nos. 5,011,769; 5,403,711; 5,660,988; and 4,876,187, and PCT published applications WO 95/05480; WO 95/1416, and WO 95/00667, and U.S. Ser. No. 09/014,304.

In particular embodiments, CPT with a probe containing a scissile linkage can be used to detect mismatches, as is generally described in U.S. Pat. Nos. 5,660,988, and WO 95/14106. In such embodiments, the sequence of the scissile linkage can be placed at a position within a longer sequence that corresponds to a particular sequence to be detected, i.e. the area of a putative mismatch. In some embodiments of mismatch detection, the rate of generation of released fragments is such that the methods provide, essentially, a yes/no result, whereby the detection of virtually any released fragment indicates the presence of a desired analyte sequence. Alternatively or additionally, the final amount of cleaved fragments can be quantified to indicate the presence or absence of an analyte sequence.

Analyte sequences of probe-representational sample nucleic acid hybrids can also be detected in a method of the invention using a sandwich assay. A sandwich assay is an amplification-based technique in which multiple probes, typically labeled, are bound to a single representational sample nucleic acid target. In an exemplary embodiment a representational sample nucleic acid target can be bound to a solid substrate via a complementary capture probe. Typically, a unique capture probe will be present for each analyte sequence to be detected. In the case of a bead array, each bead can have one of the unique capture probes. If desired, capture extender probes can be used, that allow a universal surface to have a single type of capture probe that can be used to detect multiple target sequences. Capture extender probes include a first portion that will hybridize to all or part of the capture probe, and a second portion that will hybridize to a first portion of the target sequence to be detected. Accordingly customized soluble probes can be generated, which as will be appreciated by those in the art can simplify and reduce costs in many applications of the invention. In particular embodiments, two capture extender probes can be used. This can provide, a non-limiting advantage of stabilizing assay complexes, for example, when a target sequence to be detected is large, or when large amplifier probes (particularly branched or dendrimer amplifier probes) are used.

Once a representational sample nucleic acid target has been bound to a solid substrate, such as a bead, via a capture probe, an amplifier probe can be hybridized to the fragment to form a probe-representational sample nucleic acid hybrid. Exemplary amplifier probes that can be used in a method of the invention and conditions for their use in sandwich assays are described in U.S. Pat. No. 6,355,431. Briefly, an amplifier probe is a nucleic acid having at least one probe sequence, and at least one amplification sequence. A first probe sequence of an amplifier probe can be used, either directly or indirectly, to hybridize to a representational sample nucleic acid target sequence. An amplification sequence of an amplifier probe can be any of a variety of sequences that are used, either directly or indirectly, to bind to a first portion of a label probe. Typically an amplifier probe will include a plurality amplification sequences. The amplification sequences can be linked to each other in variety of ways including, for example, covalently linked directly to each other, or to intervening sequences or chemical moieties.

Label probes comprising detectable labels can hybridize to representational sample nucleic acids thereby forming probe-fragment hybrids and the labels can be detected to determine the presence of analyte sequence. The amplification sequences of the amplifier probe can be used, either directly or indirectly, to bind to a label probe to allow detection. Detection of the amplification reactions of the invention, including the direct detection of amplification products and indirect detection utilizing label probes (i.e. sandwich assays), can be done by detecting assay complexes having labels. Exemplary methods for using a sandwich assay and associated nucleic acids that can be used in the present invention are further described in U.S. Ser. No. 60/073,011 and in U.S. Pat. Nos. 6,355 431; 5,681,702; 5,597,909; 5,545,730; 5,594,117; 5,591,584; 5,571,670; 5,580,731; 5,571,670; 5,591,584; 5,624,802; 5,635,352; 5,594,118; 5,359,100; 5,124,246 and 5,681,697.

Depending upon a particular application of the methods of the invention, the detection techniques set forth above can be used to detect representational sample nucleic acid targets or to detect targets in an amplified population of the representational sample.

The invention further provides a kit for selecting a representational sample of nucleic acid sequences from a complex mixture. The kit includes: (a) a population of capture probes complementary to a predetermined portion of the sequence collectively present in one or more nucleic acids within the complex mixture, the population of capture probes being attached to a solid support, and (b) one or more ancillary reagents.

Any of the components or articles used in performing the methods of the invention can be usefully packaged into a kit. For example, the kits can be packed to include some, many or all of the components or articles used in performing the methods of the invention. Exemplary components include, for example, capture probes, capture probes attached to a solid support, coupling reagents for coupling capture probes to a solid support, hybridization reagents, synthesis reagents, detection reagents. Any of such reagents can include, for example, some, many or all of the buffers, components and/or articles used for performing one or more of the subsequent steps for analysis of a representative sample of the invention.

One or more ancillary reagents also can be included in the kits of the invention. Such ancillary reagents can include any of the reagents exemplified above and/or other types of reagents useful in performing the methods of the invention or useful in analysis of a representative sample of the invention.

Instructions can further be included in a kit of the invention. The instructions can include, for example, procedures for making any components or articles used in the methods of the invention, performing any embodiment of the methods of the invention and/or instructions for performing any of the subsequent analysis steps employing a representative sample of the invention.

Throughout this application various publications have been referenced within parentheses. The disclosures of these publications in their entireties are hereby incorporated by reference in this application in order to more fully describe the state of the art to which this invention pertains.

It is understood that modifications which do not substantially affect the activity of the various embodiments of this invention are also included within the definition of the invention provided herein. Those skilled in the art will readily appreciate that the specific examples and studies detailed above are only illustrative of the invention. Accordingly, specific examples disclosed herein are intended to illustrate but not limit the present invention. It also should be understood that, although the invention has been described with reference to the disclosed embodiments, various modifications can be made without departing from the spirit of the invention. Accordingly, the invention is limited only by the following claims.

What is claimed is:

1. A method of selecting a representational sample of nucleic acid sequences from a mixture of nucleic acids, comprising:
    (a) providing a mixture of nucleic acids, wherein the mixture of nucleic acids comprises amplified DNA sequence;
    (b) providing a population of solid support-attached capture probes, said population comprising nucleic acids complementary to nucleic acids comprising a predetermined portion of the nucleic acid sequences collectively present in said mixture of nucleic acids, wherein said solid support comprises microspheres;
    (c) contacting said mixture of nucleic acids with said population of solid support-attached capture probes under conditions sufficient for hybridization of said nucleic acids with said capture probes, wherein the capture probes are randomly located on the solid support;
    (d) removing unhybridized nucleic acids from the solid support to separate desired sequences from undesired sequences within the mixture; thereby selecting a representational sample of nucleic acids, wherein the proportion of each sequence in said representational sample relative to all other sequences in said representational sample is substantially the same as the proportions of the sequences in said mixture;
    (e) amplifying the nucleic acids in the representational sample on the solid support to generate an amplified representational sample; and
    (f) performing a sequence analysis of the amplified representational sample.

2. The method of claim 1, wherein the mixture of nucleic acids comprises genomic DNA sequence having a complexity of at least 1.7 Gbp.

3. The method of claim 2, wherein said population of capture probes comprise sequences having complementarity to both strands of said genomic DNA.

4. The method of claim 1, wherein a representational sample has a complexity of at least 0.001% and at most 49% of said mixture.

5. The method of claim 1, wherein said mixture of nucleic acids comprises cDNA.

6. The method of claim 1, wherein step (e) comprises maintaining separation of sequences by attachment to identifiable locations on the solid support.

7. The method of claim 1, wherein performing a sequence analysis comprises SBS.

8. The method of claim 1, wherein performing a sequence analysis comprises sequencing by ligation.

9. The method of claim 1, wherein performing a sequence analysis comprises pyrosequencing.

10. The method of claim 1, wherein performing a sequence analysis comprises hybridizing a primer to a nucleic acid in the amplified representational sample and monitoring the extension of the primer by a polymerase.

11. The method of claim 1, wherein said microspheres comprise polystyrene.

12. The method of claim 1, wherein said microspheres comprise glass.

13. The method of claim 1, wherein said population of capture probes consists essentially of oligonucleotides having substantially similar melting temperatures (Tm).

14. The method of claim 1, wherein said population of capture probes comprise an amount in molar excess compared to complementary sequences within said predetermined portion of nucleic acids.

15. A method of analyzing a mixture of nucleic acids comprising:
(a) providing a mixture of nucleic acids comprising amplified DNA sequence;
(b) providing a population of solid support-attached capture probes, said population comprising nucleic acids complementary to nucleic acids comprising a predetermined portion of the nucleic acid sequences collectively present in said mixture, wherein said solid support comprises microspheres;
(c) contacting said mixture of nucleic acids with said population of solid support-attached capture probes under conditions sufficient for hybridization of said nucleic acids with said capture probes, wherein the capture probes are randomly located on the solid support,
(d) removing unhybridized nucleic acids from the solid support to separate desired sequences from undesired sequences within the mixture; thereby selecting a representational sample of nucleic acids, wherein the proportion of each sequence in said representational sample relative to all other sequences in said representational sample is substantially the same as the proportions of the sequences in said mixture;
(e) amplifying the nucleic acids in the representational sample on the solid support to generate an amplified representational sample; and
(f) detecting individual nucleic acids in said amplified representational sample to determine a sequence characteristic of said predetermined portion of the nucleic acid sequences collectively present in said mixture.

16. The method of claim 15, wherein said sequence characteristic comprises the nucleotide sequence for said predetermined portion of the nucleic acid sequences collectively present in said mixture.

17. The method of claim 15, wherein said sequence characteristic comprises the copy number for sequences in said predetermined portion of the nucleic acid sequences collectively present in said mixture.

18. The method of claim 15, wherein said sequence characteristic comprises loss of heterozygosity in said predetermined portion of the nucleic acid sequences collectively present in said mixture.

19. The method of claim 15, wherein said sequence characteristic comprises the genotype of said predetermined portion of the nucleic acid sequences collectively present in said mixture.

20. The method of claim 15, wherein said sequence characteristic comprises the methylation status of said predetermined portion of the nucleic acid sequences collectively present in said mixture.

* * * * *